United States Patent [19]

Ray et al.

[11] Patent Number: 5,046,846

[45] Date of Patent: Sep. 10, 1991

[54] METHOD AND APPARATUS FOR SPECTROSCOPIC COMPARISON OF COMPOSITIONS

[75] Inventors: James C. Ray, Mentor-on-the-Lake; Logan R. Asari, Willoughby, both of Ohio

[73] Assignee: The Lubrizol Corporation, Wickliffe, Ohio

[21] Appl. No.: 327,069

[22] Filed: Mar. 22, 1989

[51] Int. Cl.⁵ .................. G01J 3/32; G01N 21/35; G06F 15/46
[52] U.S. Cl. .................. 356/326; 250/339; 364/498
[58] Field of Search ............. 356/326, 328; 250/339; 364/498

[56] References Cited

U.S. PATENT DOCUMENTS

| | | | |
|---|---|---|---|
| 3,896,312 | 7/1975 | Brown et al. | 250/343 |
| 3,997,786 | 12/1976 | Lauer et al. | 250/343 |
| 4,102,646 | 7/1978 | Sleeter | 250/338 X |
| 4,267,572 | 5/1981 | Witte | 356/325 X |
| 4,642,778 | 2/1987 | Hieftje et al. | 364/497 X |
| 4,701,838 | 10/1987 | Swinkels et al. | 364/498 X |
| 4,766,551 | 8/1988 | Begley | 356/448 X |

FOREIGN PATENT DOCUMENTS 304232 2/1989 European Pat. Off. .

OTHER PUBLICATIONS

"Analysis of Cyclopropenoid and Cyclopropanoid Acids in Fats and Oils", by F. C. Magne, The Journal of the American Oil Chemists' Society, vol. 42, No. 4, pp. 332-336, Apr. 1965.

"Application of Cryogenic Infrared Spectrometry to the Identification of Petroleum", by P. F. Lynch et al, Analytical Chemistry, vol. 47, No. 9, pp. 1696-1699, Aug. 1975.

"Quantitative Infrared Emission Spectroscopy Using Multivariate Calibration", Analytical Chemistry I, 1988, vol. 60, No. 24, pp. 2824-2827.

"Optical Fiber Spectrometry in Turbid Solutions by Multivariate Calibration Applied to Tablet Dissolution Testing", Analytical Chemistry II, 1988, vol. 60, No. 24, pp. 2666-2671.

D. M. Haaland, "Application of New Least-Squares Methods for the Quantitative Infrared Analysis of Multicomponent Samples," Applied Spectroscopy, vol. 36, No. 6, Dec. 1982, pp. 665-672.

M. A. Maris, "Nonlinear Multicomponent Analysis by Infrared Spectrophotometry," Analytical Chemistry, vol. 55, No. 11, Sep. 1983, pp. 1694-1697.

C. W. Brown, "Accounting for Impurities in Spectroscopic Multicomponent Analysis Using Fourier Vectors," Applied Spectroscopy, vol. 40, No. 7, Sep./Oct. 1986, pp. 1023-1031.

M. F. Duvaux, "Extraction of Near Infra-Red Spectral Information by Fast Fourier Transform and Principal Component Analysis, Application to the Discrimination of Baking Quality of Wheat Flours," Journal of Chemometrics, vol. 1, No. 2, Apr. 1987, pp. 103-110.

H. Martens, "Multivariate Calibration. I. Concepts and Distinctions," Trends in Analytical Chemistry, vol. 3, No. 8, Sep. 1984, pp. 204-210.

Primary Examiner—Vincent P. McGraw
Attorney, Agent, or Firm—Robert A. Franks; Frederick D. Hunter; Forrest L. Collins

[57] ABSTRACT

A method of analysis of and an apparatus for analysing a sample comprising the steps of: (A) examining at least one characteristic of a sample as a function of a variable parameter to obtain data, (B) normalizing the data with respect to a model, (C) making a comparison of the normalized data with reference data, and (D) determining from the comparison the quality of the sample. As a function of such determination of quality, control functions may be carried out with respect to a sample that was analyzed, such as a blend sample in a chemical processing plant.

29 Claims, 11 Drawing Sheets

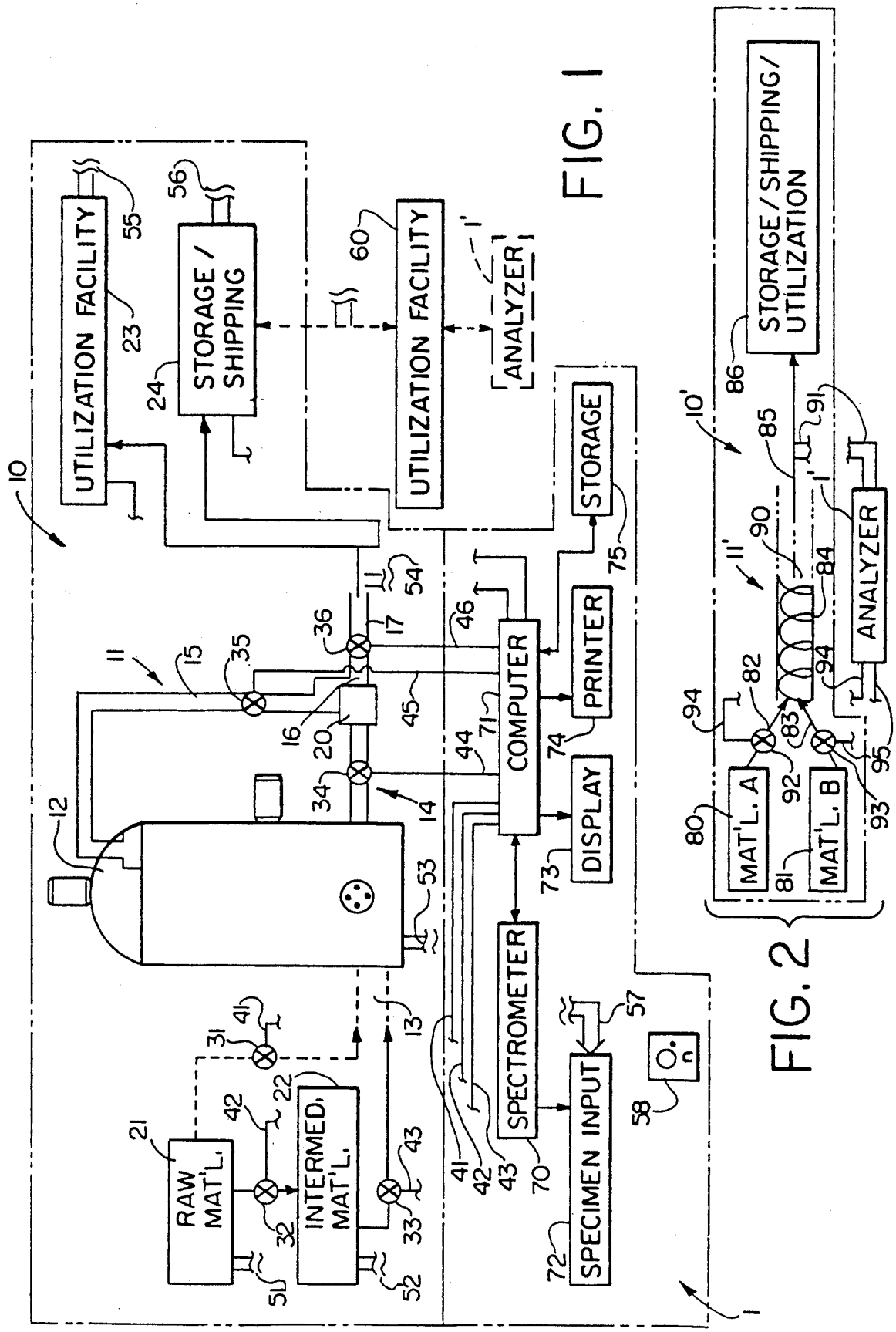

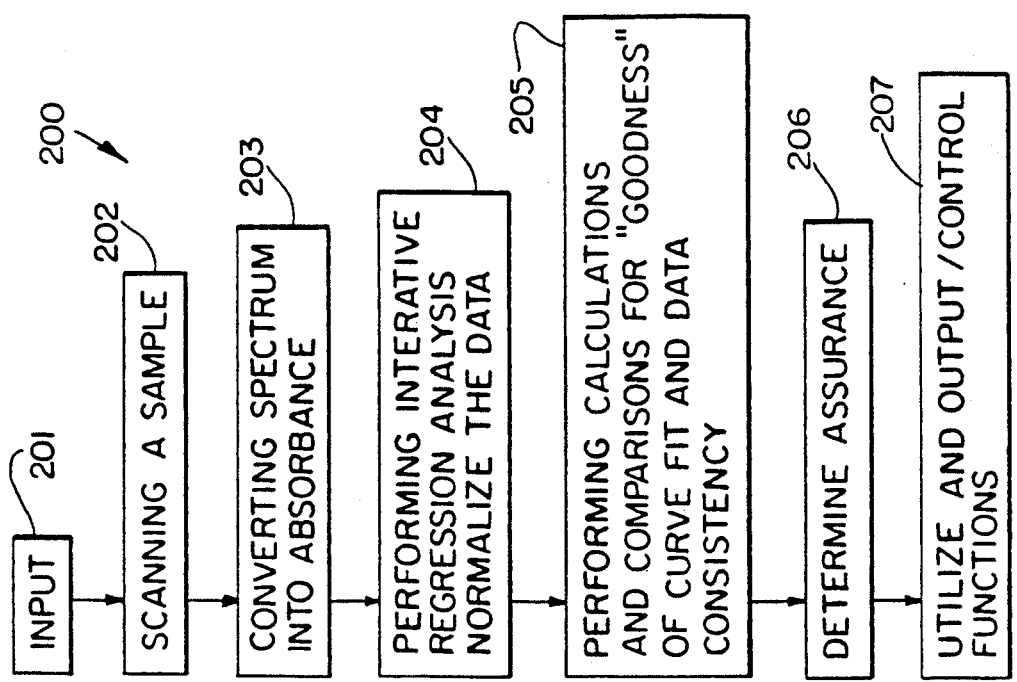
FIG. 5
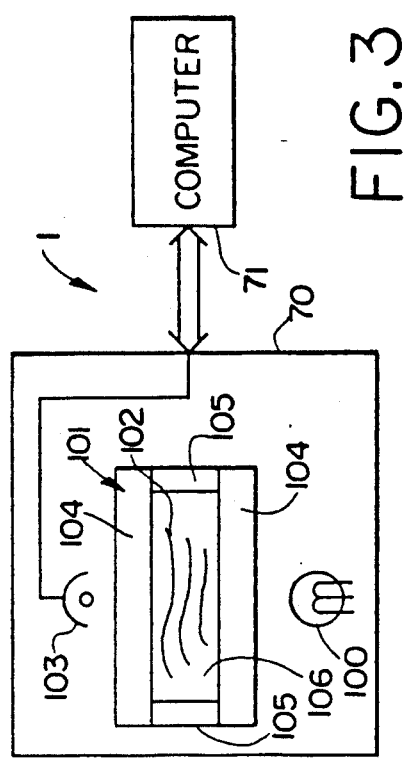
FIG. 3
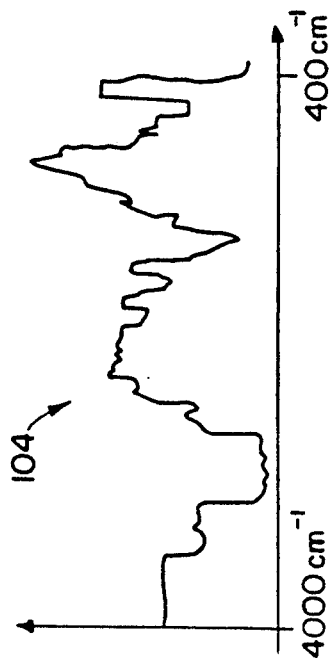
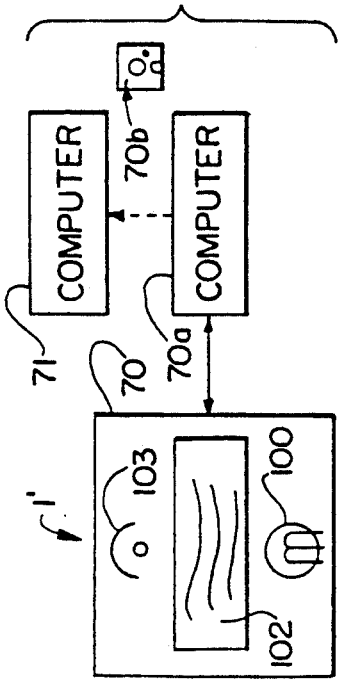
FIG. 4

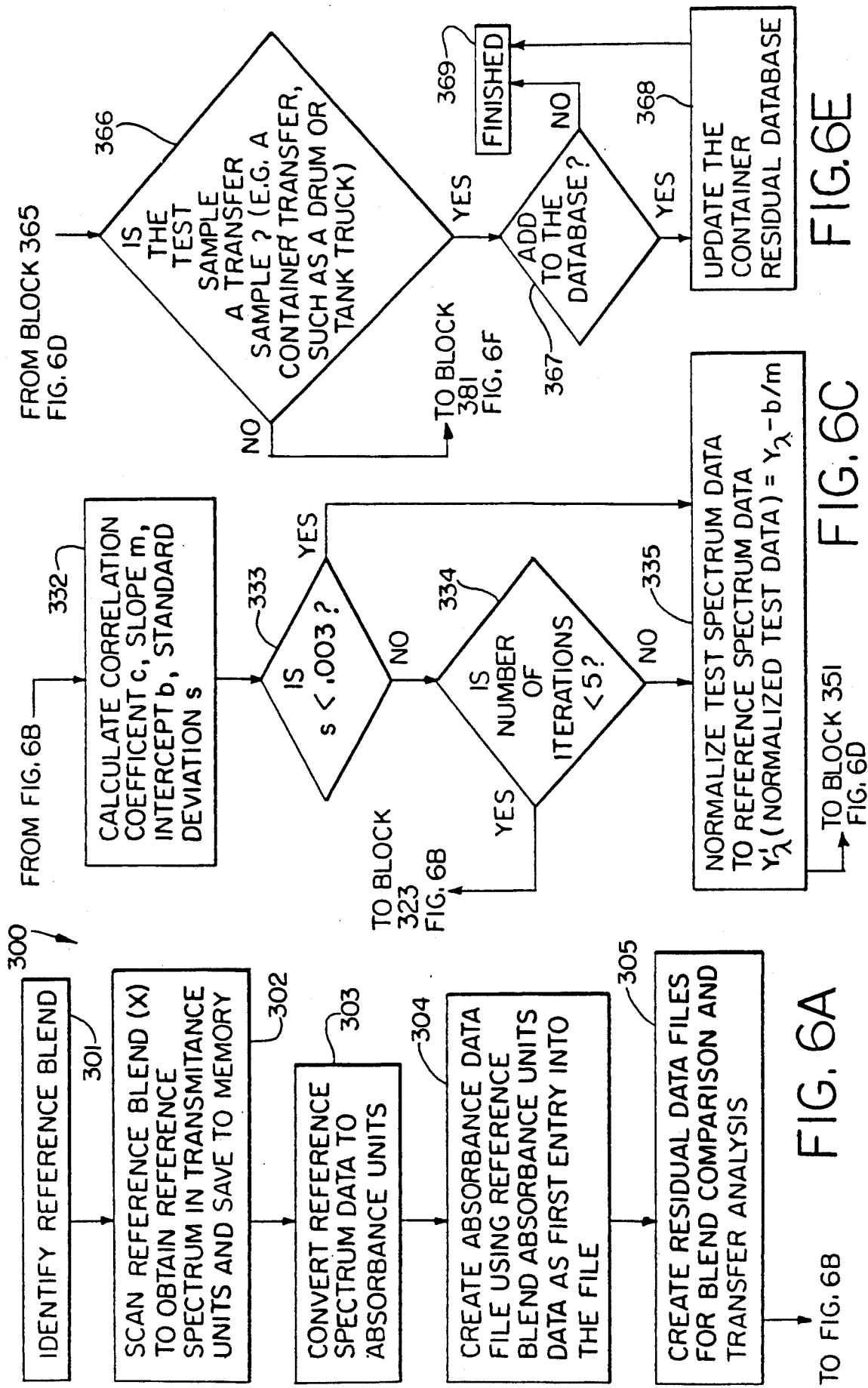

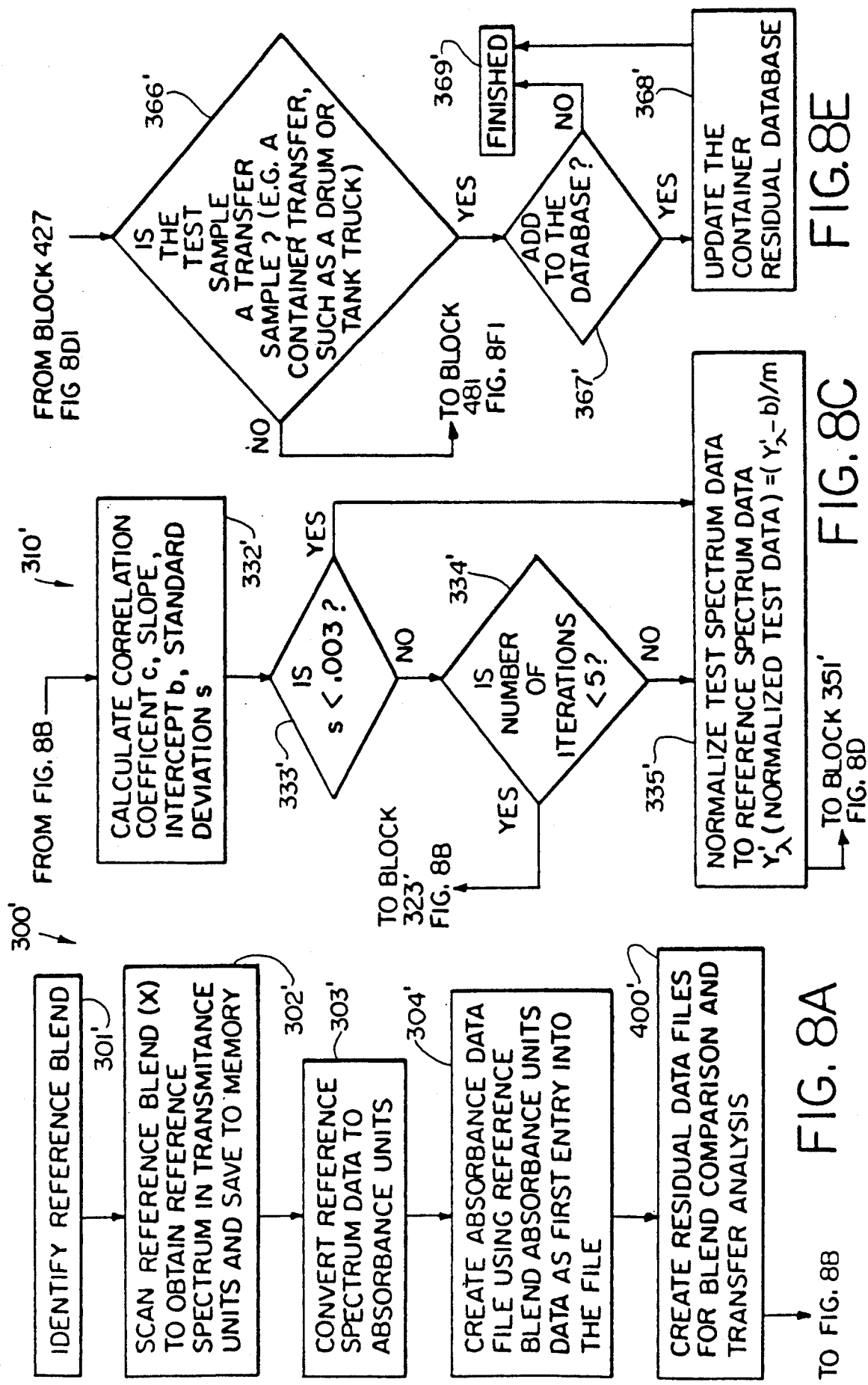

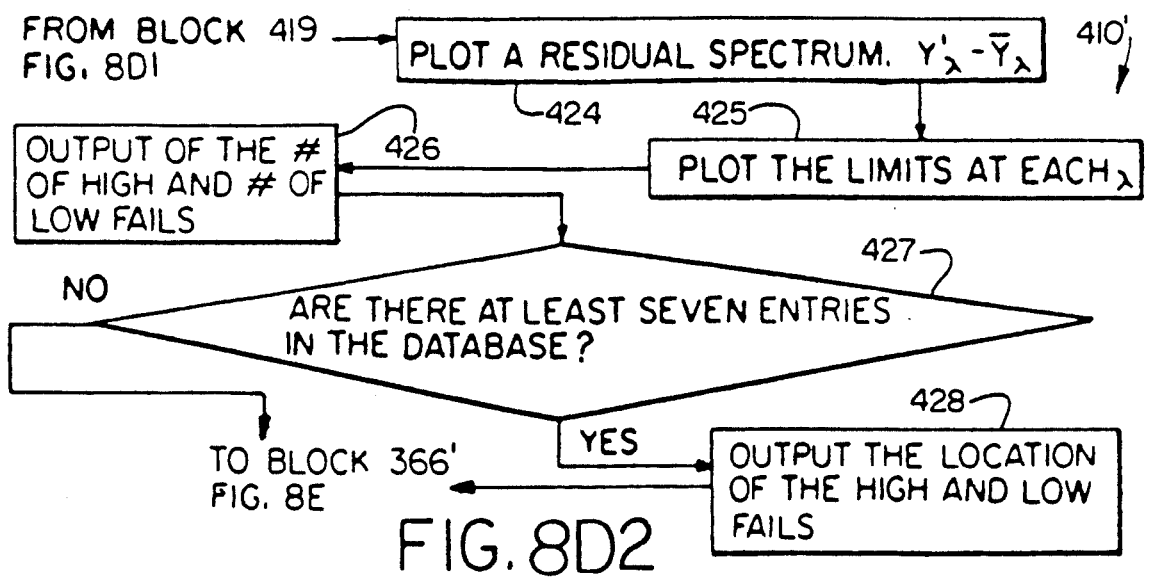
FIG. 8D2
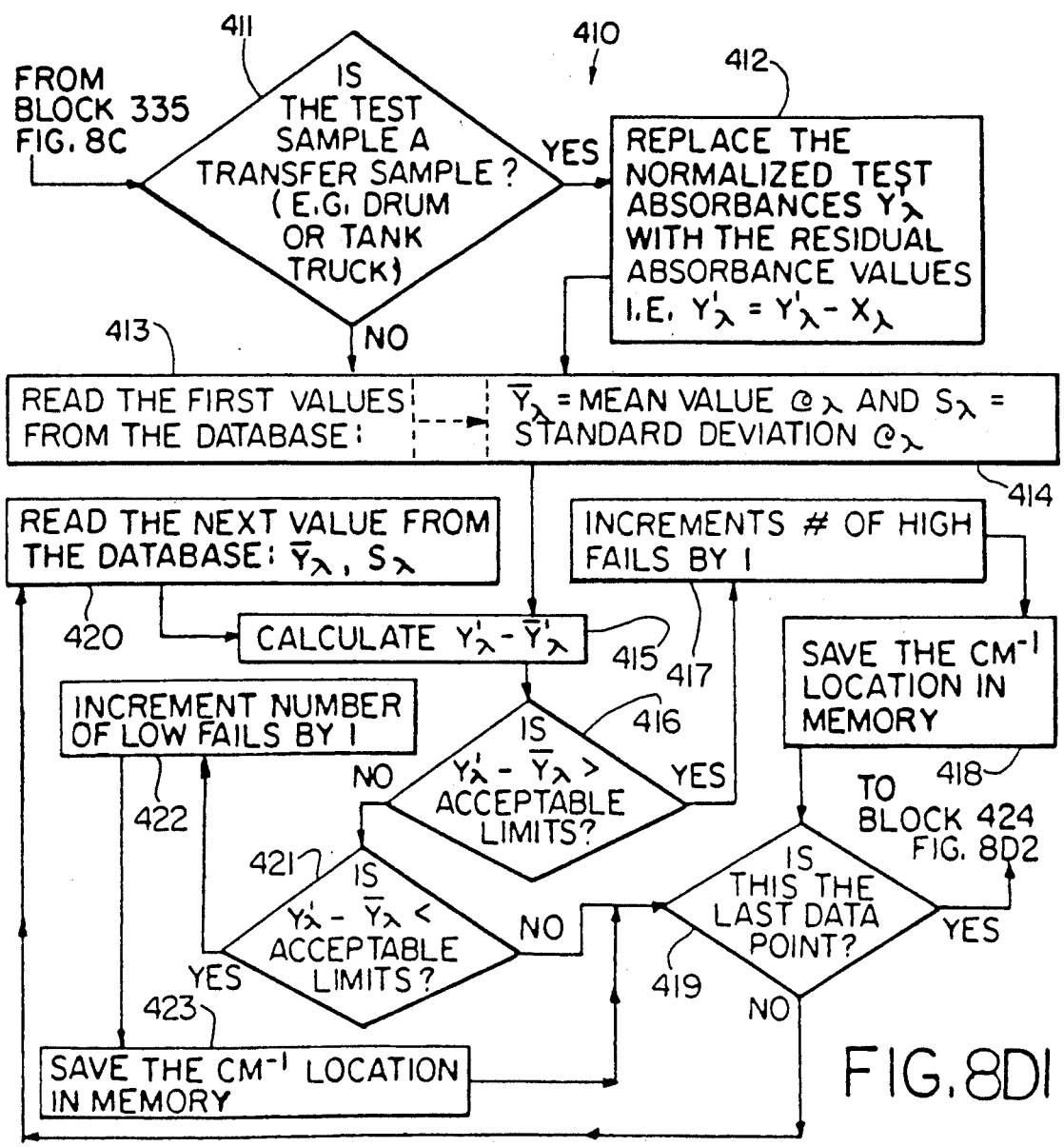
FIG. 8D1

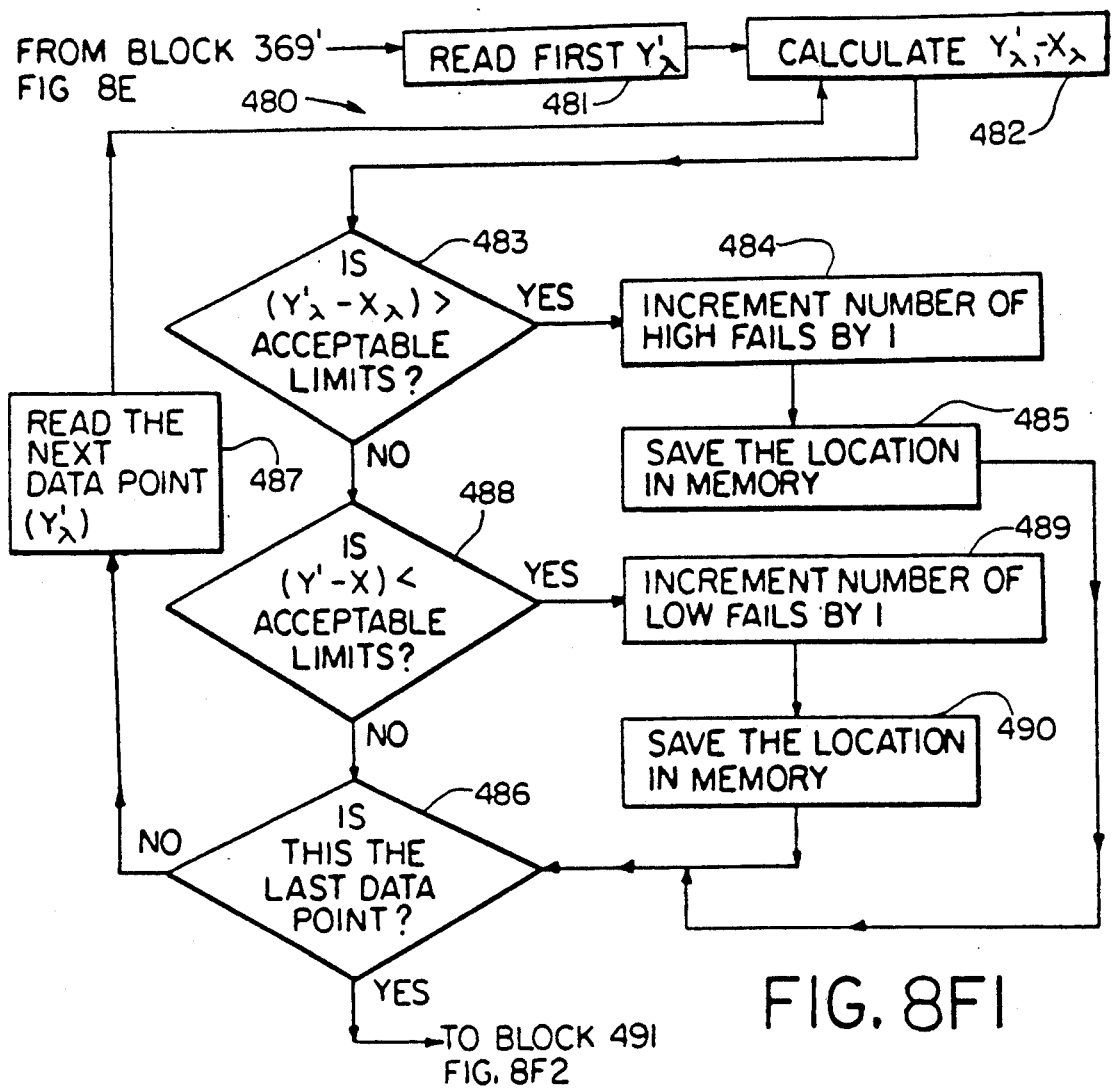
FIG. 8F1
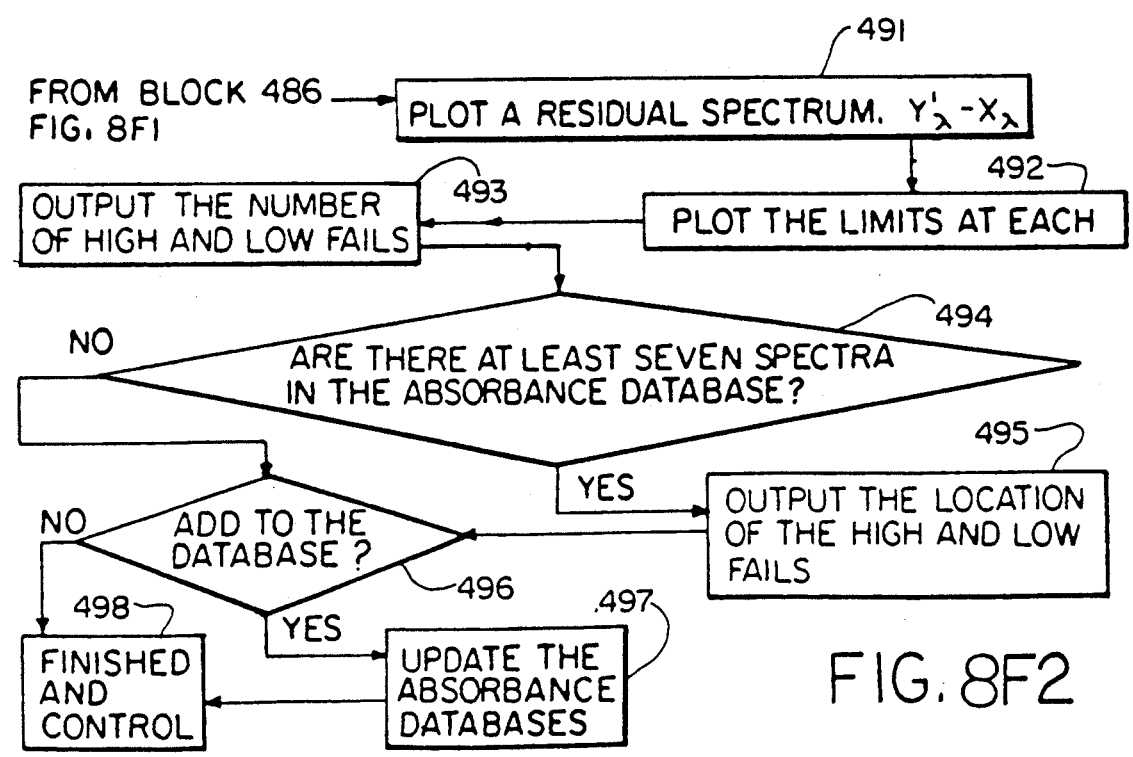
FIG. 8F2

METHOD AND APPARATUS FOR SPECTROSCOPIC COMPARISON OF COMPOSITIONS

FIELD OF THE INVENTION

The present invention relates generally, as is indicated, to a method and apparatus for spectroscopic comparison of composition, and, more particularly, to the comparison of composition to determine whether a sample composition meets one or more specifications. Moreover, the results of such comparison may be utilized according to the invention to determine and/or to control subsequent distribution and/or processing of such composition. The invention is particularly useful for comparing compositions intended to be similar, for example, one being a reference and the other being a sample intended to match the specifications or characteristics of the reference.

BACKGROUND OF THE INVENTION

Classical techniques for qualitative and quantitative analysis of compositions commonly analyze a sample for the quantity of a particular element present in a sample composition. Exemplary classical analyzing techniques have employed pH measurements, titrations, spectrophotometric and other optical examination processes, electrical processes, and so on, as is well known. Many of the classical analysis techniques disadvantageously have limited resolution. For example, two different compositions, each of which is formed of different component mixtures which provide one or more different sources of a particular element, may under a classical analysis produce a similar result, thus implying that the two compositions are the same or substantially the same. Therefore, total amount of an element, such as nitrogen, or total acidity, etc., may be determined by classical techniques; but resolution between the component parts of a molecule has not been possible using such classical techniques.

Quality control techniques that rely on the aforementioned classical analysis by comparing a sample composition to a reference composition may yield an indication that the sample is acceptable relative to the reference when in fact the sample is unacceptable, for example, being quite different from the intended specifications for the sample. Disadvantages of classical analysis techniques include the limited amount of information that can be obtained within a relatively short time, the narrow range of information obtained, and often lack of sensitivity and ruggedness of the instrumentation. A further disadvantage is the inflexibility of the instrumentation and methods employed in the past to accommodate natural and/or acceptable variations in one or more monitored parameters.

Infrared spectroscopy is a useful tool to identify individual compounds and elements of a sample material or composition. Being able to identify chemical structure, in particular, providing adequate resolution to distinguish between the component parts of a molecule, e.g., to distinguish where a particular carbon hydrogen bond exists rather than just the total amount of carbon or hydrogen, infrared spectroscopy is a good and useful tool for quality control, especially for determining whether a particular material or composition meets expected specifications therefor. Exemplary spectrometer type devices are disclosed in U.S. Pat. Nos. 3,695,764 and 3,902,807. In an exemplary spectrometer a spectrum of information representing characteristics of an examined specimen can be obtained. Such spectrum may include data representing transmittance values of electromagnetic radiation, e.g., light, through the specimen as a function of wavelength, or, more precisely by convention, wave number.

Other background information is presented in the following:

U.S. Pat. No. 4,102,646, issued to Sleeter, relates to a qualitative and quantitative method for analyzing chemical compositions for carbohydrate content using infrared spectroscopy. The analysis is directed toward fructose and dextrose in corn syrups.

U.S. Pat. No. 3,997,786, issued to Lauer, et al, relates to a system for performing on-stream analysis of chemical compositions of a chemical stream in a refinery. The analysis is performed using the principles of spectroscopy.

"Analysis of Cyclopropenoid and Cyclopropanoid Acids in Fats and Oils", by F. C. Magne, The Journal of The American Oil Chemists' Society, Vol. 42, No. 4, pp. 332-336 (Apr., 1965) relates to analysis of cyclopropenoid and cyclopropanoid fatty acid moieties and natural products using infrared spectrophotometry.

"Application of Cryogenic Infrared Spectrometry to the Identification of Petroleum", by P. F. Lynch, S. Y. Tang and C. W. Brown, Analytical Chemistry, Vol. 47, No. 9, pp. 1696-1699 (Aug., 1975) relates to the use of infrared spectrometry in identifying cured and refined petroleum products.

SUMMARY OF THE INVENTION

Briefly, the invention relates to a method and apparatus for analyzing a sample relative to a reference to determine how closely the characteristics or parameters of the sample match those of the reference. The method and apparatus of the invention are particularly useful for quality assurance of a sample, i.e., to assure the actual characteristics thereof meet the intended specifications for those characteristics. (Characteristics, parameters and specifications may be used interchangeably herein and are intended to refer to some property, ingredient, quantity, quality, etc. of the sample or reference composition or material to which the term applies, as will be evident from the description.) The method and apparatus are disclosed herein particularly with respect to infrared spectrometry techniques, which are preferred; however it will be appreciated that other analytical techniques such as, for example, spectrometry that is not limited to infrared, nuclear magnetic resonance, X-ray, microwave, liquid chromatography, gas chromatography, and so on.

The present invention is particularly useful for quality assurance analyses of compositions that have many carbon to hydrogen bonds, etc., such as additives for lubricants, fuels, and the like. However, the invention may be used for quality assurance and/or other purposes for various materials. Infrared spectrometry is particularly useful in examining materials that have a large number of carbon to hydrogen covalent bonds; examination of such materials using infrared spectrometry provides output information having high resolution and amplitude, for example, as compared to various other examination techniques for such materials.

According to one aspect of the present invention, a method of qualitative analysis of a sample relative to a reference includes (1) examining at least one characteristic of the sample as a function of a variable parameter to obtain plural data at least some of which represents such characteristic as a function of such parameter, respectively; (2) normalizing such data with respect to a model; (3) making a first comparison of such normalized data with reference data that corresponds at least in part to such model; (4) making a second comparison of such normalized data with reference data representative of at least one boundary limit for such sample; and (5) determining from at least one of such comparisons the quality of such sample relative to such reference.

According to another aspect of the invention, an apparatus for analyzing a sample relative to a reference includes (a) means for examining at least one characteristic of the sample as a function of a variable parameter to obtain plural data at least some of which represents such characteristic as a function of such parameter; (b) means for normalizing such data with respect to a model; (c) means for comparing the normalized data both with reference data that corresponds at least in part to the model and with reference data representative of at least one boundary limit for the sample. Additionally, the invention may include means for determining from at least one of the mentioned comparisons the quality of the sample relative to a reference and/or means for controlling or determining subsequent distribution or use of the sample.

As is described in further detail below, preferably the normalizing of sample data is relative to reference data and preferably the boundary limit comparison is with respect to both upper and lower boundaries for the sample.

According to another aspect of the invention, a method and apparatus are provided (I) for scanning a sample using infrared spectroscopy techniques; (II) for converting a spectrum or information concerning a spectrum obtained in the mentioned scanning into absorbance units data; (III) performing iterative regression analysis to normalize the absorbance units data to fit a model, such as a mathematical model which model also relates to reference data representative of a comparable spectrum obtained and representative of a reference or desired specifications for the sample, thus compensating for variations in optical path length, concentration and base line values; (IV) comparing the normalized data to reference data to find out how close the normalized data fits the model and also to find out differences between the normalized data and reference data; and (V) for using the results of such comparisons to determine how closely selected parameters or characteristics of the sample match the reference.

The invention is particularly useful, and, therefore, it is an object of the invention, to provide for quality assurance of a chemical mixture, composition, material or component. Based on the results of the quality assurance determination, subsequent use and/or disposition of the analyzed material may be determined and/or controlled.

According to another object of the invention, method and apparatus effect qualitative and semi-quantitative analysis of a complex chemical mixture, composition, material and/or a chemical material.

According to another object of the present invention, a process and an apparatus advantageously obtain a relatively quick and precise evaluation of the quality of a composition.

Another object of the invention is to provide insight into the actual chemical make-up of a complex chemical composition or mixture.

The foregoing and other objects, aspects, features and advantages or the present invention will become more apparent to those persons skilled in the art upon reading the details of the apparatus, method, and process, which are more fully set forth below, reference being made to the accompanying drawings and the general formulae forming a part hereof, wherein like symbols and reference numerals refer to like components and variables throughout, unless otherwise specifically stated.

It is to be understood that the invention is not limited to the particular apparatus, methods or processes described, as such apparatus, methods and processes may, of course, vary. It is also to be understood that the terminology used herein is for the purpose of describing particular embodiments only, and such terminology and the various descriptions presented herein are not intended to be limiting, since the scope of the present invention will be limited only by the appended claims and equivalents thereof.

As used in this specification and the appended claims, the singular forms "a", "an" and "the" include plural referents unless the context clearly dictates otherwise.

BRIEF DESCRIPTION OF THE DRAWINGS

In the annexed drawings:

FIG. 1 is a schematic illustration of a chemical composition blend tank and associated apparatus together with an apparatus for making spectroscopic analysis of chemical materials in accordance with the present invention;

FIG. 2 is a schematic illustration of an alternate embodiment of the invention in which the apparatus for making spectroscopic analysis is coupled with a mixing pipe;

FIG. 3 is a schematic illustration of an infrared spectrometer and an associated computer according to the present invention;

FIG. 4 is a schematic illustration like FIG. 3, but showing an alternate embodiment using plural computers;

FIG. 5 is an abbreviated flow chart depicting the process of the present invention;

FIGS. 6A through 6F is a more comprehensive computer program flow chart depicting the computation, normalization and comparison steps of the present invention;

FIGS. 8A through 8F are a modified comprehensive computer program flow chart depicting another embodiment of the computation, normalization and comparison steps of the present invention.

DETAILED DESCRIPTION OF THE INVENTION

Figure 6B:
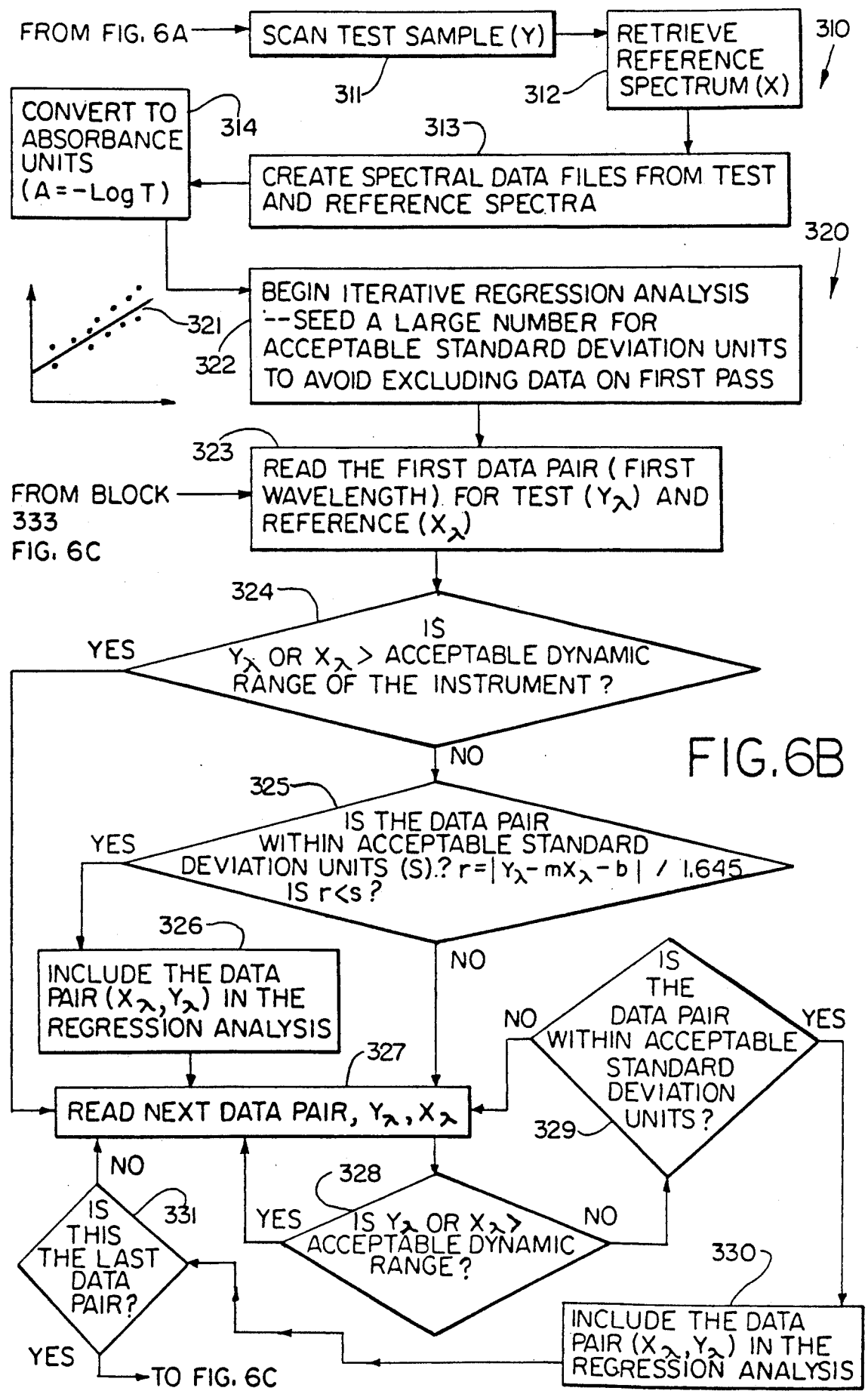

Referring, now, in detail to the drawings, wherein like reference numerals designate like parts in the several figures, and initially to FIG. 1, an apparatus for analyzing a sample is generally indicated at 1 coupled in conjunction with a chemical system 10 from which the sample is obtained. Use of the word "sample" herein indicates a material, a composition of materials, a blend of materials, a mixture of materials, and so on. Such material is a chemical, a chemical component, a chemical mixture and/or a chemical blend. Such material may be so-called raw material, even an atomic element. Such material may be so-called intermediate material which is formed of a mixture of two materials or a reaction of one or more materials and is intended for subsequent use to form a subsequent material, e.g., as a blend, mixture, etc.

Summarizing, exemplary uses of the apparatus 1 include the following. Information concerning the characteristics of a blend made in the chemical system 10 is obtained by the apparatus 1; such information preferably indicates whether the blend meets prescribed specifications. The information may be used to control the chemical system 10, e.g., to cause further blending, to add more raw material or an intermediate material (which is derived from one or more raw materials), or to discharge the blend to an outlet. The information may be used to determine whether the blend is to be processed further, is to be stored, and/or is acceptable for shipping. A record of the information may be made, e.g., stored on disk or other medium, graphed, etc.; and that record may be relied on subsequently, for example, to confirm the original specifications thereof, to compare with subsequently analyzed specifications thereof (e.g. to see whether the blend had been contaminated or damaged), etc.

Of course it will be appreciated that the specimen examined by the apparatus 1 may be other than a blend, the chemical system 10 may be other than a blend system, and other uses may be made of the analysis results.

According to the preferred embodiment the chemical system 10 is a chemical blending system 11 that includes a conventional blend tank 12 in which ingredients intended to form a final blend composition are blended or mixed. Accordingly, such blend tank 12 includes an inlet 13 for receiving input materials, an outlet 14 for delivery of blended materials out from the tank, and a feedback pipe 15 through which the blend delivered from the tank to the outlet 14 may be fed back into the tank at the top for reblending, and appropriate blending mechanism, which is not illustrated in detail but in any event is conventional. At the junction 16 of the outlet 14 and feedback pipe 15 is coupled an output pipe 17 through which the blend may be delivered from the tank for subsequent use, storage, shipping, etc., as may be desired. A pump 20 coupled to the outlet 14 may be used to pump blend received from the tank up through the feedback pipe 15 for delivery back into the top of the blend tank 12 and/or may be used to pump the blend from the tank and outlet 14 through the output pipe 17. Exemplary sources of raw material 21 and intermediate material 22 selectively connectable to the inlet 13 of the blend tank 12 are illustrated in FIG. 1 as part of the chemical system 11. Moreover, associated with the chemical system 11 are a utilization facility 23, such as a chemical plant or other facility intended to use the blend produced in the blend tank 12, and a storage/shipping facility 24, such as a storage tank, shipping container, etc., for storing or shipping the blend produced in the blend tank 12. Exemplary connections of the output pipe 17 to the utilization facility 23 and/or storage/shipping facility 24 are illustrated in the drawing.

As is seen in FIG. 1, the apparatus 1 is and/or may be coupled to the chemical system 10 at one or more locations to receive a sample for analysis and/or to control operation of the chemical system 10, for example, as a function of the results of an analysis made by the apparatus 1. Such control is exemplified by connections to a number of flow control valves 31–36. Other control devices also may be used alone or in conjunction with such valves. Such connections 41–46 are, for example, electrical connections on which electrical signals may be provided to the respective flow control valves 31–36 to cause opening or closing thereof.

Briefly summarizing operation of the apparatus 1 in conjunction with the chemical system 10, connections or sampling points 51–56 are located throughout the chemical system 10 and may be selectively coupled to the apparatus 1, as at a connection 57 thereof, and/or may be used for obtaining a sample from the location in the chemical system 10 for delivery to the input 57 of the apparatus 1, i.e., without a direct fluid connection to the input 57. The apparatus 1 analyzes the sample received. The results of the analysis may be used to assure that the quality of the sample meets certain specifications, such as those of a reference material, to provide information for use in controlling operation and/or fluid flow in the chemical system 10, to provide automatic control of the respective flow control valves 31–36 via appropriate signals on the connections 41–46, respectively, and so on. For example, based on analyses of samples taken at locations 51, 52 or 53, changes may be made in the amount of raw material, intermediate material, blending, etc. used in the chemical system 10. Furthermore, analysis of a sample from location 54 in the output pipe 17 may be used to determine whether the blend delivered from the blend tank 12 meets desired specifications of a reference blend. Also, analysis of a sample from location 55 may be used to provide information indicating whether the blend employed at the utilization facility 23 still corresponds to, i.e. meets the specifications of, the reference blend and/or that which was delivered to the utilization facility via the output pipe 17 and, for example, initially sampled at location 54 and analyzed by the apparatus 1 piror to delivery to the utilization facility 23.

Another important aspect of the invention is the ability to analyze the blend at location 54 prior to delivery of the blend to a storage and/or shipping facility or container 24 followed by the sampling at location 56 of the blend composition contained in the tank 24, for example, to confirm promptly upon filling such container or in the future that the characteristics of the blend material in the container still meet the desired specifications. Additionally, the information concerning the nature and specifications of the material delivered to the container may be stored, say in a data storage medium, such as a computer disk or the like, which is represented at 58 in FIG. 1. Subsequently at a remote utilization facility 60 (say, at another chemical plant, for example) the blend material or composition in the shipping container 24 may be tested by a further analyzer apparatus 1' (primed reference numerals designating parts similar to those designated by unprimed reference numerals) to confirm that the blend material received by and/or used at such remote utilization facility 60 still meets the desired specifications. The latter check may be made with respect to data which is sent to the remote facility 60 and analyzer apparatus 1' thereof on the disk 58, which may be shipped with the container 24. In this way one can assure that the quality of the blend material employed at the utilization facility 60 meets the desired specifications of the blend material produced in the blend tank 12.

As is seen in FIG. 1, the apparatus 1 includes a spectrometer instrument 70 and a computer 71. The spectrometer preferably is an infrared spectrometer that produces output information that can be used to distinguish various characteristics of the sample, both in terms of amplitude of output and resolution between respective components or constituents of the sample. A specimem input 72 is provided the spectrometer 70 and furnishes an appropriate sample for examination by the spectrometer, either in the form of a static or fixed fluid cell into which a sample is placed for examination or fluid flow cell through which a fluid flows as it is being examined. The spectrometer 70 may include a computer which controls the operation of the spectrometer. Alternatively, the computer 71 may be used for analysis control. Furthermore, the computer 71 is used for data processing, i.e., to operate on and to analyze the data or information obtained by the spectrometer 70. The results of such operation and analysis by the computer 71 may be displayed on a display 73, printed by a printer 74, and/or stored in a storage medium, such as a disk dive or the like, 75. The computer 71 also is connected to provide electrical signals on leads 41-46 to the various control valves 31-36 as was described above to operate the same and, accordingly, to provide an operational control function for the overall chemical system 10. Details of the apparatus 1, including specifically the spectrometer 70 and computer 71 will be described in greater detail below with reference to FIGS. 4-7.

Turning briefly to FIG. 2, an alternate embodiment of the invention is illustrated. In the alternate embodiment an apparatus 1', which includes a spectrometer, computer and the other components of the apparatus 1 described above with reference to FIG. 1, is coupled to a chemical system 10'. The system 10' includes sources of materials 80, 81, flow paths 82, 83 from the respective sources of material, a mixing pipe 84, and an outlet pipe 85. The outlet pipe 85 is coupled to a downstream storage, shipping, and/or utilization facility 86. The materials from the sources 80, 81 are supplied to the mixing pipe 84 in which they are mixed, for example by a mixing auger 90, and the mixed or blended material is supplied via the outlet pipe 85 for storage or shipping or utilization at 86. Utilization may be, for example, as a component in the chemical process; shipping may be to a remote site for storage and/or utilization; and storage may be for subsequent utilization.

The analyzer apparatus 1' is used to analyze a sample of the mixed or blended material from the outlet pipe 85; for this purpose a connection 91 is schematically illustrated. Such connection may be a flow through connection; alternatively, such connection may be a conventional sampling of material from the outlet pipe and transporting of the sample to the analyzer apparatus 1' for appropriate analysis. Respective flow control valves 92, 93 are coupled in the inlet lines 82, 83, respectively, to control the flow of ingredients from sources of materials 80, 81. The analyzer apparatus 1' is coupled, as by electrical connections 94, 95, to the respective flow control valves to control such flow as a function of the analysis made of the sample by the analyzer apparatus. In addition to such flow control and/or instead of such flow control, the analyzer apparatus 1' may be used simply to assure that the quality of the blended or mixed material in the outlet pipe 85 meets the desired specifications, to provide a record thereof, and/or to provide information for comparison when the blended or mixed material subsequently is utilized either at the chemical system 10, utilization apparatus 86 or at a remote utilization site.

Referring, now, to FIG. 3, a spectrometer 70 is schematically illustrated. The spectrometer 70 may be any of a variety of commercially available spectrometers; preferably it is an infrared spectrometer. More preferably, the spectrometer 70 is a Fourier-transform infrared spectrometer to achieve the desired resolution and amplitude of output information. Exemplary spectrometers are Perkin-Elmer 780, 880, 1600 and 1700 series. Most preferably the spectrometers are Perkin-Elmer 782 or 1700 spectrometers.

Such an infrared spectrometer 70 typically would include a source of infrared radiation 100, a sample cell 101 for containing a sample 102 intended for analysis, and a photosensitive detector 103 able to detect electromagnetic radiation received from the cell over a broad infrared spectrum of, for example, from about 4000 $cm^{-1}$ to about 400 $cm^{-1}$ (wave numbers). In the illustrated embodiment the source 100, cell 101 and detector 103 are arranged to detect the amount of electromagnetic energy transmitted through the cell 101 (and sample 102 therein), i.e. transmittance values. As is conventional, the spectrometer 70 includes means, not shown, to relate such transmittance values to wavelength or wave numbers. Information representative of electromagnetic radiation received by the photodetector 103 as a function of wavelength or wave number is provided the computer 71.

Although the preferred source 100 produces electromagnetic energy or radiation in the infrared portion of the optical spectrum and the detector 103 is appropriately responsive to detect energy in that portion, it will be appreciated that the spectrometer may be operative in other portions of the electromagnetic spectrum. It should be noted that infrared radiation is just used to exemplify the broad invention.

An exemplary graph representing the output from the spectrometer 70 is indicated at 104 in FIG. 3. Such graph 104 represents a spectrum for a sample analyzed by the apparatus 1. Such spectrum includes transmitance values with respect to wave numbers over a range, for example, from 4000 to 400 $cm^{-1}$. Such spectrum may be processed by the computer 71 according to the invention, as is described in greater detail below.

The sample cell 101 may be a conventional one either of the flow through or static (fixed) type. Typically the cell would include a pair of plates 104 and spacers 105 which cooperate to define an interior volume 106 within which the sample 102 is placed. An inlet port (not shown) and possibly an outlet if the cell were a flow through type also would be provided, as is conventional. Preferably the plates 104 and spacers 105 are formed with precision in order to provide an accurate path length for transmission of infrared radiation through the cell 101. The plates 104 should be transparent to the radiation of the source 100 intended for detection by the detector 103. Exemplary plates would be of salt material. Alternatively an ATR (attenuated total reflectance) cell or other cells may be used in the spectrometer.

The computer 71 may be a conventional personal computer, microcomputer, minicomputer, main frame computer or the like. A programmed data processing means or a programmable data processing means other than a computer also may be employed. The purpose of the computer 71 is to interact with the spectrometer 70 to obtain useful information, to operate on data received from the spectrometer 70, and to provide an output in the form of information, a record, and/or a control function that is dependent on the information or data received from the spectrometer 70.

As is seen in FIG. 1, the computer 71 coupled directly to the spectrometer 70 is able to provide the computer functions required by the spectrometer 70 as well as the data analysis and output functions. Alternatively as shown in FIG. 4, the spectrometer 70 may include a computer 70a which is dedicated to servicing the needs of the spectrometer to obtain useful data or information representative of the examined sample; and the computer 71 may be coupled directly to the computer 70a or may receive data therefrom via an appropriate data transfer mechanism, such as a disk, tape, modem connection, etc., represented at 70b, to process the data for analysis purposes.

The preferred spectrometer is an FT (Fourier Transform) type which scans all wavelengths at one time; then the computer 71 (or computer 70a in FIG. 4, which is part of the spectrometer 70) converts the scan information to spectrum information in the form of transmittance values. Alternatively, a dispersive type spectrometer may be used, which obtains a complete recording of the desired spectrum, as is well known.

The apparatus 1 and 1' in accordance with the invention as described above is intended to be exemplary. Other types of apparatus for obtaining data about characteristics of a sample may be utilized. For example, other types of spectrometers may be utilized and/or other types of computers may be utilized.

Turning to FIG. 5, a flow chart representative of the method of the invention is represented at 200. Such method may be summarized, as follows.

At block 201 an input is provided. Such input is in the form of a sample of a composition intended to be analyzed by the apparatus 1. Such sample may be provided from one of the connections 51-56 of FIG. 1, for example.

At block 202 the sample is scanned using the spectrometer 70, for example, in order to obtain a spectrum representing the characteristics of interest of the sample. An exemplary spectrum is depicted at 104 in FIG. 3. Preferably the scanning is in the infrared region from about 4000 to 400 cm$^{-1}$. A preferred range is between 2500 to 500 cm$^{-1}$. A most preferred range is between 1900 and 600 cm$^{-1}$, which encompasses what is frequently referred to as the "fingerprint region".

As is depicted in FIG. 3, a preferred spectrometer is one that measures light transmission through a sample. Therefore, at block 203 the transmission information or spectrum is converted to absorbance units and a spectrum representing absorption characteristics of the sample. An advantage to such conversion is the simplification of Beer's law on which subsequent processing of the information is based in accordance with the present invention. More specifically, according to Beer's Law, absorbance (A) of light as a function of wavelength equals the multiplication product of the molar extinction coefficient (e or epsilon) of the material being examined at the specified wavelength, the concentration (c) of the ingredient in question in the sample being examined, and the path length (l) of light through the sample, as follows:

$$A_{lambda} = \text{epsilon } cl \qquad \text{Equation 1}$$

Equation 1 for Beer's Law in absorbance is a linear equation. Absorbance and transmittance (T) are related logarithmically according to Equation 2 below:

$$A_{lambda} = -\log T_{lambda} \qquad \text{Equation 2 ps}$$

Thus, according to equation 2 above, the absorbance of light of a given wavelength is equal to the negative logarithm of the transmittance of light at the given wavelength.

The advantage to converting transmittance units to absorbance units at block 203 is the simplification of the use of Beer's Law in the linear equation form thereof. Alternatively, if desired, transmittance values may be utilized in which case the more complex non-linear form of Beer's Law would be employed in processing the data. (This is contemplated by and included in the present invention.)

At block 204 the absorbance units data is normalized. Normalization in the preferred embodiment includes two parts, one is an effort to match the absorbance units data to a model and the second is the exclusion of data that clearly does not fit the model. The preferred model is a mathematical one representing a linear function, and this is possible due to the convenient linear relation of Beer's Law in absorbance units. Such normalizing, then, in effect becomes a curve fitting procedure, e.g. fitting data to a straight line. The preferred curve fitting procedure is achieved using iterative regression analysis.

Continuing in FIG. 5, at block 205, calculations are performed on the normalized data, and two comparisons are made. One comparison is to determine the "goodness" of curve fit achieved in block 204. The second comparison is to determine the data consistency, more particularly, to determine whether the normalized data or groups of such data match corresponding data representing a reference level or reference specification. As is described in greater detail below, such reference specification can be a dynamic one, being updated periodically as a function of acceptable data representing a particular sample being scanned in the process of the invention.

At block 206 the quality of the sample relative to the reference is determined to see whether the sample falls within the desired specifications therefor. Such quality assurance determination is based on the comparisons made in block 205.

The desired specifications are criteria which define products of acceptable characteristics. The criteria are set to allow the inclusion of products which have a normal variation of product characteristics. Similarly, the criteria excludes products with data which is a nonnormal deviation from the reference. For instance, it has been found that criteria of the mean absorbance of the reference plus or minus from 1 to about 6 times standard deviation are acceptable for the purpose of the present invention. Criteria of from about 2 to about 4 times standard deviation are preferred. Most preferred criteria are about 3 times standard deviation.

At block 207 the quality assurance determined information from block 206 is utilized. Such utilization may be in the form of effecting control of one or more flow control valves, or the like. Alternatively and/or additionally, such utilization may include the providing of output information to indicate how the blend in output pipe 17, for example, is to be disposed. e.g. utilized in one process or another, re-blended, scrapped, etc. Such utilization also may be in the form of providing a record representing the quality of the sample so that when the material subsequently is used, that record is relied on to see whether the sample still meets the same specifications or has been overheated, contaminated, etc. Finally, such utilization may be in the form of updating information stored about acceptable reference specifications.

The method of the invention illustrated in and described above with reference to FIG. 5 is illustrated in detail with respect to the system flow chart/computer program flow chart combination in FIGS. 6A through 6F. As to those portions of the chart of FIG. 5 and flow chart of FIGS. 6A-6F which may be carried out by computer 71, for example, a person having ordinary skill in the art of computer programming with some understanding of the nature of the data to be received and processed, e.g., that data from the spectrometer 70, would be able in a reasonable period of time to write a computer program in an appropriate language, such as C, BASIC, etc. The actual computer program code that would be prepared may vary from programmer to programmer. However, the code would follow, as is conventional, the steps outlined in the flow charts of FIGS. 6A-6F, for example, which serve as a shorthand representation of such computer program, as is well known.

In FIG. 6A is a start-up flow chart 300 for the apparatus 1 of the invention. Such start-up flow chart provides for the obtaining of reference information or a so-called reference database representative of acceptable specifications which are desired to be matched by the sample blend produced in the chemical system 10. In the event that reference data is already available to the user of the apparatus 1, then the steps set forth in the start-up flow chart 300 may be skipped as long as such reference data and the residual data files noted in flow chart 300 are otherwise made available for subsequent use described below with reference to FIGS. 6B through 6E.

In flow chart 300 of FIG. 6A, at block 301 a reference blend material is identified. Such reference blend may be a material that is well known to have certain properties. Such reference blend may be a laboratory sample the characteristics of which already have been carefully established. Such reference blend may be a material that has certain desirable characteristics, even though the reasons for having such characteristics are not known.

A reference database for use in the normalizing and comparison steps subsequently described must be developed. Such reference database is obtained in blocks 302, 303 and 304. At block 302 the reference blend is scanned using the spectrometer 70. Such scanning preferably is in the range of from 1900 cm$^{-1}$ to 600 cm$^{-1}$, although other ranges may be used, as was mentioned elsewhere herein. Scanning could be over the full infrared range of 4000 cm$^{-1}$ to 450 cm$^{-1}$; but most of the useful information in the instant invention would be in the fingerprint region of 1900 cm$^{-1}$ to 600 cm$^{-1}$, and limiting the scan range would reduce the amount of memory required and time required for the data and data processing according to the invention. The scan data in the form of transmittance values is stored. Then, at block 303 the spectral data representing the transmittance values obtained in block 302 is converted to absorbance units. Absorbance units are preferred herein in view of the linear relationship of Beer's law in absorbance units, which is described above.

At block 304 an absorbance units reference data file is created. The first entry in the file would be the absorbance units just obtained. Additional entries would be made in the future to update the reference file using data from subsequent acceptable analyses of samples that meet desired specifications. The absorbance units reference data file would include data points representing absorption with respect to wavelength, as is conventional in infrared spectrometry.

Residual data files for blend comparison and possible transfer analysis if the sample is intended for containerization and/or shipment, are created at block 305. Such residual data files may be used for subsequent comparisons and/or verifications as is described elsewhere herein.

In FIGS. 6B is presented the sample obtaining flow chart portion 310, which includes blocks 311, 312, 313 and 314 in which an absorbance spectrum of the sample is obtained. Initially, at block 311 the test sample is scanned using the spectrometer 70 to obtain transmittance data. A scan range in the mid infrared region is used, i.e., from 1900 cm$^{-1}$ to 600 cm$^{-1}$, although a broader, narrower or different range may be used. Preferably, though, the range over which the sample is scanned should be the same as the range over which the reference was scanned to facilitate comparing the sample and reference information.

At block 314 the transmittance data for the sample is converted to absorbance units to enable using the linear form of Beer's law.

A brief summary of the application of Beer's law to the instant invention follows. For each of the reference and the sample, Beer's law would apply such that absorbance at a particular wavelength equals the product of the molar extinction coefficient at that wavelength for the material being examined, the concentration of that material, and the path length through the material. The general formula for Beer's law with respect to wavelength is:

$$A_{lambda} = e_{lambda} * c * 1,$$

where $A_{lambda}$ is absorbance at wavelength lambda; e is the molar extinction coefficient at the specified wavelength; c is the concentration of the chromophore, i.e., that which absorbs the electromagnetic radiation; and 1 is the path length through the material.

For a mixture, which includes several components, Beer's law with respect to wavelength can be re-written, as follows:

$$A_{lambda,i} = 1 * \Sigma(e_{lambda,i} * c_i),$$

where i is the number of components over which the summation is taken.

Keeping in mind the foregoing, then, Beer's law can be applied to compare two spectra, namely a reference spectrum and a sample spectrum by rewriting the above equations, as follows: For the reference (ref)

$$A_{lambda,ref} = 1_{ref} * (e_{lambda,i} * c_i) + a_{ref}$$

and for the sample (sam)

$$A_{lambda,sam} = 1_{sam} * (e_{lambda,i} * c_i) + a_{sam}$$

In the two equations just above, the variables are as previously identified. The values $a_{ref}$ and $a_{sam}$ are constants which relate to baseline absorbance characteristics.

According to the invention it is intended that the mixtures or blends forming the reference and forming the sample will be similar. Therefore, for the two mixtures the summation $e_{lambda,i}*c_i$ is relatively constant. Accordingly, such summation term can be solved for in the reference equation just above, as follows:

$$\Sigma e_{lambda,i}*c_i = (A_{lambda,ref} - a_{ref})/l_{ref}$$

The last equation can be substituted into the sample equation above to achieve, the following:

$$A_{lambda,sam} = l_{sam}*((A_{lambda,ref} - a_{ref})/l_{ref}) + a_{sam}.$$

The latter equation can be rewritten, as follows:

$$A_{lambda,sam} = (l_{sam}/l_{ref})*A_{lambda,ref} + (a_{sam} - (l_{sam}/l_{ref}))*a_{ref}.$$

The latter equation is linear and is in the form $$y = m*x + b$$

i.e., the equation for a straight line. The term y is absorbance [$A_{lambda,sam}$]. The slope of the line m is a function of the ratio of the two path lengths, respectively, through the sample and reference [$(l_{sam}/l_{ref})$]. The y intercept, b, is a function of the base line absorbance values, ($a_{sam}$ and $a_{ref}$) and the path lengths through the sample and reference [$(a_{sam} - (l_{sam}/l_{ref})*a_{ref}$], all of which are constants during a given scan. Therefore, by matching the scan data to a model which represents a straight line, variations in path length and in base line absorbance can be automatically compensated and the effect thereof cancelled.

Since there may be different path lengths each time a sample or reference is scanned, and since there may be different base line absorbance values each time a scan is made, utilizing the above techniques to cancel out the effects of those variations which are not representative of the characteristics of the examined material is particularly helpful to facilitate the comparisons according to the inventions while maintaining accuracy of results.

Importantly, since the sample data and reference data can be related according to the equation Y=mx+b, if the intercept b and the slope m are known, then for each absorbance value of the reference material "x" the corresponding absorbance value of the sample material "y" would be a function of the slope times the value "x" offset according to the y intercept b. Using iterative regression analysis (especially iterative linear regression analysis) techniques the data representing absorbance values of the sample can be matched to the model according to the invention. Iterative regression analysis techniques are well known; they will be summarized below.

In the iterative regression analysis procedure portion 320 of the flow chart in FIGS. 6B and 6C, essentially efforts are made to match the sample spectrum data to a straight line, which is represented at 321 of FIG. 6B. Data points occur on both sides of the line, and an effort to best fit the line to the data is made using the iterative regression analysis; to do this reliance on conventional standard deviation techniques are used. Additionally, in the iterative regression analysis, data which is beyond the dynamic range of the instrumentation is excluded or dropped from the collection of data subsequently used for the balance of the iterative regression analysis.

The iterative regression analysis will be used to derive several values. The values are "c" which is a correlation coefficient, "m" which is the slope of the line mentioned above, "b" which is the intercept of the line mentioned above, and "s" which is standard deviation. Equations for these values in terms of $x_{lambda}$ (reference) and $y_{lambda}$ (sample) and "n", which represents the number of data pairs ($x_{lambda}$ and $y_{lambda}$), that are within the dynamic range of the instrumentation are presented below:

$$c = \frac{(n*\Sigma(x_\lambda*y_\lambda)) - (\Sigma x_\lambda)*(\Sigma y_\lambda)}{\sqrt{((n*\Sigma(x_\lambda)^2) - (\Sigma x_\lambda)^2)*(n*\Sigma(y_\lambda)^2) - (\Sigma y_\lambda)^2}}$$

$$m = \frac{(n*\Sigma(X_\lambda*Y_\lambda)) - (\Sigma X_\lambda)*(\Sigma Y_\lambda)}{(n*\Sigma(X_\lambda)^2) - (\Sigma X_\lambda)^2}$$

$$b = \frac{\Sigma Y_\lambda - m*\Sigma X_\lambda}{n}$$

$$s = \sqrt{\frac{\Sigma((Y_{lambda} - b/m) - X_{lambda})^2}{n}}$$

wherein m is slope; b is the x-axis intercept; c is the coefficient of correlation; and n is the number of data pairs (X;Y), wherein Y, X, r and s are as defined previously.

The above equations are standard ones used for linear regression analysis, which is the preferred regression analysis according to the invention in view of the linear relation of Beer's law described above. However, it is possible that the regression analysis could be carried out according to a non-linear function due to the fact that the best model to which the data can be expected to fit would be a non-linear model; in such case different equations could be used, as would be evident to those having ordinary skill in the art.

At block 322 the iterative regression analysis is begun. For iterative regression analysis a test will be made to determine whether data is within certain standard deviation unit values, as is well known. To assure that during the first pass in the iterative regression analysis no data is excluded due to exceeding standard deviation value, a large number initially is seeded as the initial acceptable standard deviation value below which value data will be retained for consideration in the next iterative regression analysis pass. Exemplary initial values seeded may be 5 or greater, which, is is well known in standard deviation and iterative regression analysis mathematics, will assure that the data will not be excluded.

At block 323 the first data pair is read. Such first data pair is at a first wavelength (lambda) for the test sample ($Y_{lambda}$) and for the reference ($X_{lambda}$). For example, such first wavelength may be at the wave number 1900 $cm^{-1}$. Subsequent data pairs read will be at other wavelengths.

An inquiry then is made at block 324 to see whether $Y_{lambda}$ or $X_{lambda}$ is in the acceptable dynamic range of the instrument. For a dispersive spectrometer instrument such dynamic range would be about 1.0 absorbance unit; and for the preferred fourier transform (FT) spectrometer instrument such dynamic range would be about 2.00 absorbance units. Dynamic range is the range of the instrument where the response conforms to the model. For instance, the dynamic range of the infrared spectrometers is that range where absorbance and concentration have a linear relationship.

If the data pair is not within the dynamic range of the instrument, then at block 325 an inquiry is made to determine whether the data pair is within acceptable standard deviation units (s). In the initial pass through the flow chart portion 320, recall that the standard deviation units value is seeded as a rather large number, e.g., greater than 5, which should include all data. In subsequent passes through the flow chart portion 320, the actual standard deviation units value will be calculated (as is described below according to the equation for "s" written above), and it is likely that such calculated standard deviation units value will be smaller than 5. To eliminate some of the data, though, a number "r" is calculated, such that $$r = |(((Y_{lambda}-b)/m) - X_{lambda})/1.645|$$

The number "1.645" is selected according to well known standard deviation techniques to eliminate ten percent of the data. A larger number would include more of the data and would require more passes through the iterative regression analysis to achieve the desired closeness of curve fit to the straight line equation mentioned above; a smaller one would include less data and would be somewhat less accurate than the described preferred ten percent.

If the value "r" is less than the standard deviation units value "s", and this would be the case for the initial pass through the flow chart portion 320, then at block 326 the data pair is selected for inclusion in the regression analysis. That is, such data pair $X_{lambda}$, $Y_{lambda}$ would be selected for inclusion as the regression analysis is continued.

At block 327 the next data pair ($X_{lambda}$, $Y_{lambda}$) is read. Block 327 is reached either directly from block 324 (if $Y_{lambda}$ or $X_{lambda}$ is greater than the dynamic range of the instrument), from block 325 (if the data pair ($X_{lambda}$, $Y_{lambda}$) is not within the acceptable standard deviation units value), or from block 326 (if the last read data pair ($X_{lambda}$, $Y_{lambda}$) had been included in the regression analysis).

An inquiry is made at block 328 to see whether in such data pair $Y_{lambda}$ or $X_{lambda}$ exceeds the acceptable dynamic range of the spectrometer instrument. If yes, then a loop line is followed back to block 327 and the next data pair is read (until the last data pair has been read). However if at block 328 the data pair is within the acceptable dynamic range of the instrument, then at block 329 another inquiry is made to determine whether the data pair is within the acceptable standard deviation units value currently being used; note initially such value is 5 and, therefore, such data pair will be expected to fall within such value.

If at block 329 the data pair did not fall within the acceptable standard deviation value, then a loop line would be followed back to block 327. However, if the data pair does fall within the acceptable standard deviation units value at block 329, then at block 330 the data pair ($X_{lambda}$, $Y_{lambda}$) is included in the regression analysis. Then, at block 331 an inquiry is made to determine whether the data pair currently under consideration is the last data pair in the spectrum being analyzed; if negative, then a loop line is followed back to block 327 and the next data pair is considered.

After the last data pair ($X_{lambda}$, $Y_{lambda}$) has been considered and either included or not in the group of data being analyzed for fitting a straight line curve thereto, while discarding extraneous data that either is beyond the dynamic range of the spectrometer instrument or (on subsequent passes through the iterative regression analysis after the first pass) is outside the standard deviation units value limits, then at block 332 the values for correlation coefficient c, slope m, intercept b, and standard deviation s are calculated according to the formulae presented above.

The correlation coefficient c is used for detecting goodness of fit of the curve to the data; more particularly, the correlation coefficient c indicates whether at each data point the value of Y (absorbance of the sample) is the same or different (and how different) from the value X (absorbance of the reference). The value c can vary between 0 and 1. If the correlation coefficient c equals 1, then there is a perfect fit of all the Y data points to the X data points; if the value c is close to 0, then there would be a relatively large difference between most of the data points Y and X for each wavelength.

The slope m and intercept b are used for normalization steps described further below. The standard deviation s is used to eliminate or to discriminate between data, e.g., to eliminate about ten percent of the data in each pass through the iterative regression analysis procedure of the flow chart to try to obtain a relatively good straight line curve fit to the remaining data.

At block 333, then, an inquiry is made to determine whether the standard deviation is less than 0.0030. (The value 0.0030 is based on experience indicative of the acceptable tolerance of matching the sample data to a linear curve. The value could be larger or smaller. If smaller, then less data would be accepted on each pass through the regression analysis portion 320 of the flow chart. Therefore, for closer tolerance the value 0.0030 would be reduced to a smaller number. If broader tolerance is acceptable, then the number may be increased, and this would probably reduce the number of passes that would be necessary through the regression analysis portion 320 of the flow chart to achieve an acceptable curve fit to the data. Thus, it will be appreciated that the value 0.0030 can be varied to determine the quality of the output information versus the speed of execution of the process to obtain a usable output.

If at block 333 the value of s is larger than 0.0030, then the iterative regression analysis may be continued, depending on the result of the inquiry made at block 334 to determine whether the number of iterations, i.e., passes through the iterative regression analysis portion 320 of the flow chart is less than five. If affirmative, then a loop line is followed back to block 323, and the next pass through the iterative regression analysis portion 320 of the flow chart is made; this time, though, there is a different value for the standard deviation number s, i.e., that which had just been calculated at block 332, so that it would be expected that about ten more percent of the data would be excluded to further refine the data and have a better likelihood of closely matching a straight line thereto.

For if at block 333 the standard deviation s is less than 0.0030, then at block 335 normalization occurs. More specifically, at block 335 a normalized data value for each absorption data point for the sample as a function of wavelength is calculated. Such calculation is according to the following equation:

$$Y_{lambda} = (Y_{lambda} - b)/m,$$

wherein $Y_{lambda}$ is the value of the absorbance of the sample at the wavelength in question, m is the slope of the best curve just fit to the data, and b is the "y" intercept of that curve. More specifically, the slope m is the ratio of the path length through the specimen ($l_s$) the path length through the reference ($l_r$), and the "y" intercept, b, is a function of the base line cell clarity with respect to the reference, namely $[a_s-(l_s/l_r)a_r]$, wherein the values $a_s$ and $a_r$ are the absorbance value of the cell without the respective sample or reference therein, namely the clarity of the cell, which values are constants.

Using such normalization technique, then, it will be appreciated that the normalized data values of absorbance $Y'_{lambda}$ take into consideration possible variations in path length and base line values so that such normalized data can be readily compared with the reference data, as is discussed further below. Such normalization is important to the invention in that it overcomes problems experienced in infrared spectrometry due to cell differences, i.e., differences in path length and base line values which may vary as a function of cell preparation, for example.

The normalized absorbance values $Y'_{lambda}$, i.e., for each wavelength at which the sample was examined by the spectrometer 70, (this is referred to as the normalized sample spectrum) is retained in memory for subsequent comparison with the reference data values (referred to sometimes as the reference spectrum).

Figure 6D:
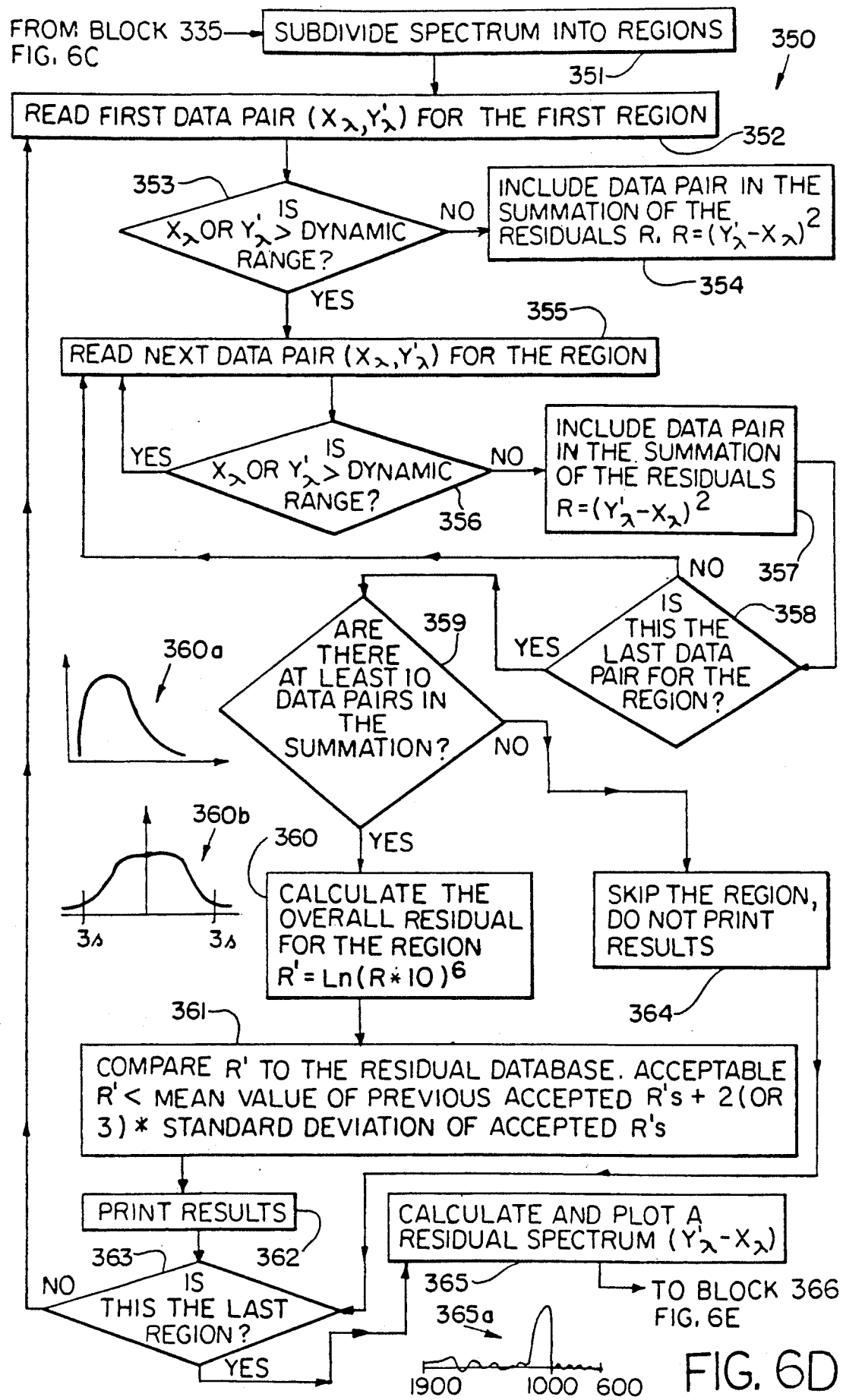

Turning, now, to FIG. 6D, a flow chart portion 350 by which a Residual Mean Squared (RMS) database is developed to determine the goodness of curve fit to the data available is followed. Beginning at block 351 the data is subdivided into regions. Each region of the data, i.e., of a graph plotted according to the data obtained, may represent a particular component of the blend of interest. Accordingly, if a problem appears in a particular region, then it is understood that the problem is due to a problem in the particular component that would cause a particular absorbance at the particular wavelength in question. The question answered at each region is whether the data in that region meet the criteria of the reference for such region.

At block 351, as well as, elsewhere in this method, it is useful to divide the data into regions by wavenumber. Although the calculations as described herein may be performed on regions of 1 wavenumber or less, it is convenient to divide the data into regions. Regions of 1 to about 200 wavenumbers are convenient regions. It should be noted that as the size of the region increases the resolution of the method decreases. For regions of large wavenumbers, the variation of absorbance at a given wavelength values is somewhat masked by the number of absorbance corresponding to acceptable criteria. Preferably, the regions are up to about 500 wavenumbers, more preferably from 1 to about 200 wavenumbers, and most preferably about 5 to about 100 wave numbers.

At block 352 the first data pair ($X_{lambda}$, $Y'_{lambda}$) for the region is read. In the preferred embodiment the sample and reference are scanned between 1900 $cm^{-1}$ and 600 $cm^{-1}$; and the number of regions into which the data obtained over that range is thirteen. The regions may be more or less; and the regions may be the same size, i.e., wavelength span, or different. The important relationship, though, is that each region represents a particular component or group of components of interest in the blend that would affect light at the wavelength(s) occurring in such region.

At block 353 an inquiry is made to see whether either one of the components of the data pair $X_{lambda}$, $Y'_{lambda}$ is greater than the dynamic range of the instrument. If not, then block 354 is followed to cause the data pair to be included in the summation of the residuals, R, where $$R = (Y_{lambda} - X_{lambda})^2,$$

for example. The value of R may be determined by the opposite difference squared or by the absolute value of either difference not squared. The reason for squaring the difference or for taking the absolute value is to obtain a value that can be part of a sum of values that do not cancel each other as a function of sign, i.e., positive and negative. Instead, due to the squaring function or the absolute value function, the number value for R always is a positive number so that a final value indicative of the degree of curve fit is obtained.

Block 355 next is followed, either from block 353 or from block 354, depending on whether the data pair values were within the dynamic range of the spectrometer 70. At block 355 the next data pair ($X_{lambda}$, $Y'_{lambda}$) for the region under study is read. At block 356 a check is made to determine whether the data is within the dynamic range of the spectrometer instrument. If outside dynamic range, then a loop line is followed to read the next data pair at block 355. If within dynamic range, then at block 359 the data pair is included in the summation of the residuals, as was the case at block 354. Then, at block 358 an inquiry is made to determine whether the data pair is the last one for the region; if not, then a loop line is followed back to block 355 to read the next data pair ($X_{lambda}$, $Y'_{lambda}$).

If the last data pair for the region has been detected at block 358, then at block 359 an inquiry is made to determine whether there are at least ten data pairs in the summation of residuals for that region. If affirmative, then the overall residual value for the region is calculated according to the equation $$R' = ln((R/(n-2))*10^6)$$

The multiplier of $10^6$ is to make the numbers more customary instead of being very small. The logarithmic transformation is needed because of the statistical analysis of the RMS values which would follow a curve as is indicated at 360a in FIG. 6D in order to provide a curve 360b where a mean value can be determined. Thus the logarithmic transformation converts the curve 360a to the curve 360b. Moreover, such transformation also enables a determination of standard deviation values that can be used to determine whether the curve 360b is acceptable for the region in question.

More specifically, at block 361 a comparison is made of the R' value to the residual database. The basis for determining an acceptable R' value is that the value R' must be less than the mean value of previous accepted R's plus 2 (or 3) times the standard deviation of the previous accepted R's. The multiplier 2 or 3 determines how close a fit is required; whether a region must be very close to the curve for that region or may be not so close in matching the parameters for that region. At block 362 the results are printed for the region under studY. An example of such a print out is presented in Chart I, just below:

| Region | CHART I<br>ln(RMS*10$^6$) | Limit |
|---|---|---|
| 1900-1800 | 1.01776 | 6.06105 |
| 1800-1700 | .582234 | 4.335319 |
| . | | |
| . | | |
| . | | |
| **1100-1000 | 6.48771 | 6.38571 |
| etc. | | |

From Chart I, in which three regions of thirteen are shown, the first two regions are acceptable according to the comparison in block 361 of the transformed formed residual R' relative to the mean value of previous accepted R's plus 2 or 3 times the standard deviation of previous accepted R's. For example, the value 1.01776 is less than the limit of 6.06105. On the other hand, for the region at 1100 cm$^{-1}$, the transformed residual R' is 6.48771, which is larger than the limit 6.38571; therefore, this region demonstrates a failure and may indicate that the component, such as a particular ingredient of the blend, does not meet specifications therefor. As before, whether the 2 or 3 times multiplier is used to derive the limit values, will be determined by how close a tolerance is required of the sample to the reference.

The information from Chart I above may be relied on by a user of the apparatus 1 to determine whether or not a particular valve should be open or closed in the chemical system 10; whether a sample is acceptable, etc. Moreover, a simple computation can be made using the computer 71 to determine whether any components are out of specification, and, if so, whether that component warrants a certain automated opening or closing of one of the valves illustrated in FIG. 1, e.g., to add or to reduce the amount of an ingredient to the blend, to direct the blend to the outlet pipe, to direct the blend to waste, to continue to cause blending in the blend tank, etc.

At block 363 an inquiry is made to determine whether the region just under examination is the last one; if not, then a loop line is followed back to block 352. Block 363 also can be reached via blocks 359 and 364 if there are not at least ten data pairs in the summation of the residuals; such number of data pairs ordinarily (although not necessarily) is required to have an adequate sampling of data to be able to rely on the data. If enough data is not included in the region, then the region is skipped, and the results are not printed, for there may not be enough information fully to evaluate the region. Of course, if there are no regions in which data is printed because there is not enough data to be evaluated, then there also would be considered to be a failure of the sample to meet specifications, for example, or, alternatively, that there is a failure in the equipment of apparatus 1 and/or 10.

Next, at block 365 a residual spectrum is calculated and plotted. Such residual spectrum is the value $Y'_{lambda} - X_{lambda}$ as a function of wavelength lambda. Such graph is illustrated schematically at 365$a$ in FIG. 6D. Note the large peak at about 1000 cm$^{-1}$, which is the location of the unacceptable region corresponding to the data in Chart I above. Such graphical presentation of the residuals spectrum facilitates seeing what regions may be unacceptable in meeting the desired specifications of the sample with respect to the reference. Thus, from the printed results obtained in block 362 and from the graphical presentation of such results, a person would be able to discern or a machine would automatically be able to determine whether the sample meets specifications or not and also would, for example, provide an automatic control function based on whether such specifications were met and, if desired, to what extent met.

At block 366 (FIG. 6E) an inquiry is made to determine whether the sample under consideration is a transfer sample. A transfer sample is one that is intended for delivery to a drum, tank or tank truck for storage or for transporting to another location. If affirmative, then the information obtained earlier maY be used as a record for subsequent checking on the nature of the sample, either when the sample reaches its destination in the tank truck, when the drum is opened for subsequent use of the sample, etc. The sample then can be re-examined using the apparatus 1, then, and the results can be compared with the original data for the sample to determine whether the sample still is in good condition for use, e.g., not being contaminated, overheated, etc.

If the sample is a transfer sample, then at block 366 the flow chart follows to block 367. An inquiry is made at block 367 to determine whether to add the data representing the transfer sample to a container or transfer sample residual database. Such container or transfer residual database is based on data that is approved (or disapproved) for shipment to a customer, for example; by adding data to such database, one is able to tighten the database to reduce variability in the samples. Added data increases the ability to pick up, i.e., to discern, abnormal contaminant in a transfer sample. Thus, if the answer at block 367 is yes, then the container residual database is updated, and the flow chart/program finishes until the next sample has to be analyzed. Also, by updating the residuals database, it is possible for the overall values of data in that database to vary from the original values; this tends to tighten up the database and to reduce the amount of fluctuation that can be acceptable in a sample relative to the specifications of the reference.

The finished program at block 369 now has determined whether the transfer sample has met the desired specifications established by the reference or by reference data that had been stored over time, i.e., over several sample runs of the program flow chart of FIGS. 6A through 6E just described.

If at block 366 it was indicated that the sample is not a transfer sample, then it must be a flow sample or a blend sample in the blend tank 12 (FIG. 1).

The first comparison according to the invention is described above with reference in particular to FIG. 6D to check on goodness of curve fit. A second comparison is made in the flow chart portion 380 illustrated in FIG. 6F to compare the normalized absorbance test data to the absorbance database, which is the average absorbance at each particular wavelength (lambda) for all scans that have gone into the database. This comparison takes into account inherent variability per region. If the results of such comparison is unsatisfactory in one or more regions, depending on the region(s) in question and/or the degree that a region is out of specification, the computer 71 may automatically adjust one or more of the flow valves of FIG. 1 to alter the blend sample, to re-blend the sample, to discard the sample, etc.

At block 381 the first $Y'_{lambda}$ value is read for use in the comparison to be made, as is described below. Such comparison is to the absorbance database to determine acceptability of the normalized value of the reference absorbance at the specified wavelength, namely $Y'_{lambda}$. The criterion for acceptability is that the value $Y'_{lambda}$ must lie between the mean absorbance value for that wavelength (over all the absorbance values in the absorbance database at that time plus or minus 2 or 3 times the standard deviation of the absorbance value at the specified wavelength. The multiplier 2 or 3 is determined by experience to indicate how large a deviation would be acceptable between the normalized value of $Y'_{lambda}$ and the absorbance of the reference $X_{lambda}$, i.e., at such wavelength.

At block 382 an inquiry is made to see whether the normalized absorbance of the sample at the particular wavelength $Y'_{lambda}$ is greater than the acceptable limits, i.e., is $$Y_{lambda} > \overline{X}_{lambda} + 2[or\ 3] * s,$$

where $\overline{X}_{lambda}$ is the mean value of absorbance in the absorbance database at the specified wavelength and s is standard deviation of the absorbance data in such database at such wavelength.

If the answer at block 382 is negative, then another inquiry is made to determine whether the normalized absorbance of the sample at the particular wavelength $Y'_{lambda}$ is less than the acceptable limits, i.e., is $$Y_{lambda} < \overline{X}_{lambda} \pm 2[or\ 3] * s$$

If the answer to the inquiry made at block 383 is negative, then at block 384 an inquiry is made to determine whether the data point just read is the last one. If not, then at block 385 the next normalized value $Y'_{lambda}$ for the next wavelength is read, and a loop line returns back to block 382.

Moreover, if at block 382 the answer was affirmative, i.e., the $Y'_{lambda}$ value were greater than acceptable limits, then at block 386 a counter of the number of high fails is incremented by one; at block 387 the location of the wavelength where the failure occurred is saved to memory, and the program flows to block 384 to determine whether the last data point had been read.

If at block 383 the answer was affirmative, i.e., that the $Y'_{lambda}$ value were less than the acceptable limit, then at block 388 a counter of low fails would be incremented by one and the location of the wavelength at which such failure occurred is saved in memory at block 389. The flow chart then flows to block 384, as above.

If at block 384 it is determined that the last data point has been read, then at block 390 a residual spectrum is calculated and plotted. Such residual spectrum is the value of the normalized absorbance value for the sample at each wavelength minus the mean absorbance value from the database of all prior specimens (or at least selected ones) that had been tested to date and found to be worthy of including in the absorbance database, e.g., since such data did adequately match the specifications of the reference. Such calculation and plotting, then is of the relationship:

$Y'_{lambda} - \overline{X}_{lambda}$ as a function of wavelength.

The limits or boundaries for the sample absorbance values, particularly the normalized values as plotted in block 390, are then plotted in block 391. Specifically, the mean value of the absorbance database for the particular wavelength plus and minus 2 [or 3] times the standard deviation of the absorbance data in the database at such wavelength are plotted. These boundaries are those with which the normalized data is to be compared. If the normalized data exceeds such boundaries, e.g., just exceeding the boundaries, or exceeding the boundaries by at least a prescribed amount, or exceeding the boundaries at a prescribed number of wavelengths or at specific one or more wavelengths, then this information can be relied on to determine the acceptability of the blend sample and can cause a control function to occur using the computer 71 to adjust one or more of the valves to control the processing of the chemical sample in the blend tank 12, etc. See the graph in FIG. 7.

Turning to block 392, an inquiry is made to determine whether at least seven spectra have been stored in the absorbance database. Note that the absorbance database is the reference against which samples may be compared according to the invention. Ordinarily the samples that have been included in the absorbance database are those which had successfully been compared to the reference information and found favorably to meet specifications of the reference information. The selection of at least seven spectra to have been included in the reference absorbance database is arbitrary; but experience has shown that at least seven samples are required to have an adequate statistical sampling of data to obtain a statistically significant result using the invention. The actual number checked at block 392 may be more or less than seven, depending on experience, e.g., the nature of the tests and materials with which the apparatus 1 is used, and so on.

If the answer at block 392 is affirmative, then at block 393 the number of high and low fails and the wavelength locations of each are printed; such information had been obtained at blocks 386–389 described above. This information can be used for diagnostic purposes to identify the cause of a problem with a particular sample. For example, if there is a high fail at a particular wavelength, then it may indicate that the blend material had been overheated during processing, and so on.

Figure 6F:
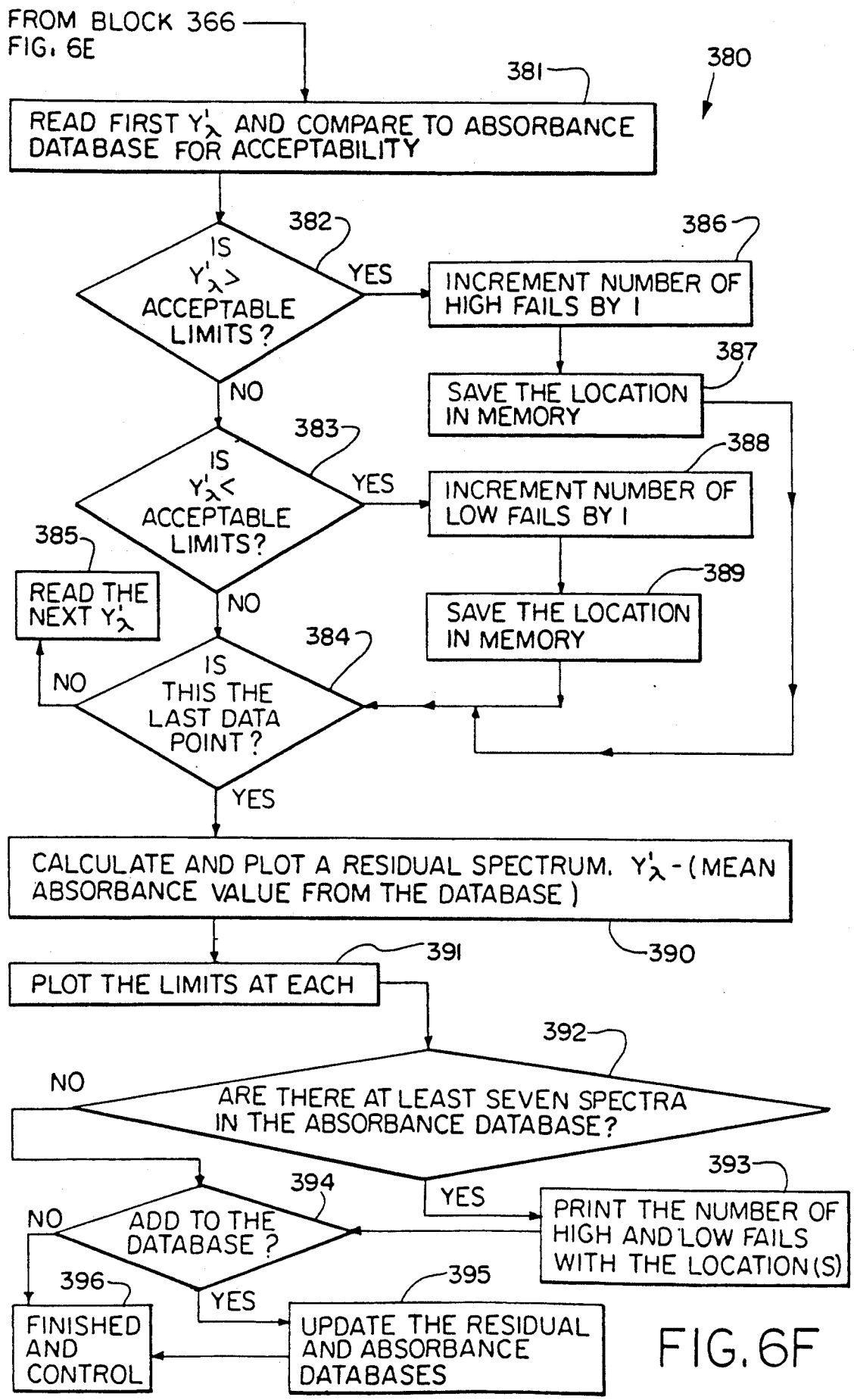
Figure 7:
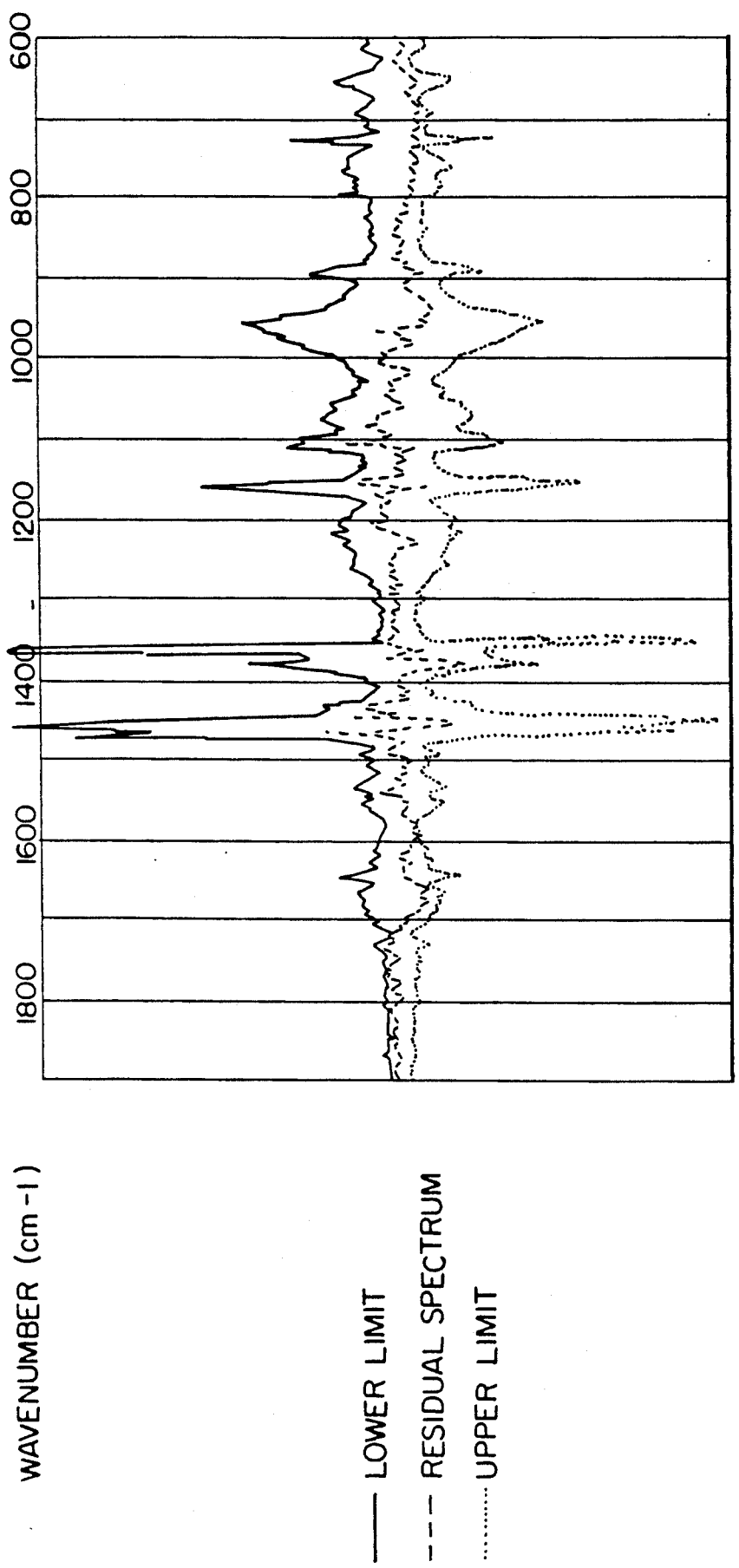
FIG. 7 is a graphical representation of an absorbance spectrum relative to upper and lower limits therefor.

At block 394 an inquiry is made whether the recent data is to be added to the absorbance database. Such decision may be based on experience, which would indicate whether the sample spectrum adequately matches that of the reference and therefore meets specifications, or may be automatically according to numerical and/or artificial intelligence parameters and data processing in the computer 71, for example, based on similar criteria as experience. If at block 392 there were less than seven spectra in the absorbance database, then block 393 would be bypassed via a loop line to block 394, as is illustrated in FIG. 6F.

Following block 394, at block 395, assuming the data is to be added to the absorbance database, then at block 395 the residual and absorbance databases are updated. Such updating importantly provides some variation in the reference data values as a function of gradual and/or natural changes which are acceptable deviations and changes in the nature of the sample over time. Thus, the apparatus has the capability of providing dynamic reference information for comparison with subsequent samples.

At block 396 the program flow chart finishes until the next analysis is made. Such finishing may include simply a printing out and/or storing of data obtained in the above-described analysis. Alternatively, and preferably, such finish would include a feedback control of one or more of the flow control valves of FIG. 1 in order to alter the nature of the chemical system 11 and the chemical process/industrial process being carried out therein.

Turning to FIGS. 8A through 8F, a modified flow chart which is similar to the flow chart depicted in FIGS. 6A through 6F, is illustrated. The flow chart of FIGS. 8A through 8F represents a shorthand presentation of a computer program that may be prepared in an appropriate computer language to carry out another embodiment of the invention.

A general comparison of the different techniques exemplified in the flow charts of FIGS. 6A through 6F with those of FIGS. 8A through 8F can be made as follows. In the former, comparisons are made on a regional basis in FIG. 6D and limits are established based on a residual spectrum ($Y'_{lambda} - \overline{X}_{lambda}$) (where $Y'_{lambda}$ is the normalized absorbance data value at respective wavelengths and $\overline{X}_{lambda}$ is the mean absorbance value from the database). In the latter (FIGS. 8A–8F), comparisons are made of the individual normalized absorbance values at the respective wavelengths with the mean data vale of all prior acceptable absorbance values (at such respective wavelengths) previously obtained and stored with respect to other "runs" of the apparatus 1 and limits are established based on a residual spectrum ($Y'_{lambda} - X_{lambda}$) (where $X_{lambda}$ is the actual absorbance data value of an acceptable reference intended to be matched by the sample). The comparisons made in the flow charts of FIGS. 8A through 8F enable more comprehensive data analysis than those of FIGS. 6A through 6F because more points are compared (i.e, the data is not grouped into large regions for comparison. In this embodiment, comparisons are made on regions having the same regions as those described for FIGS. 6A–6F. It is preferred in this embodiment to use regions having 1 to about 10 wavenumbers with 1 to about 5 wavenumbers preferred. A clearer look at the data is obtained to determine whether the data is going askew with natural variations.

Rather than repeating the description and function of the several steps and/or boxes of the flow chart of FIGS. 8A through 8F, which steps and/or boxes depicted therein are the same or substantially the same as corresponding steps and/or boxes described above with reference to the illustration of FIGS. 6A through 6F, it will be understood that the various boxes illustrated in FIGS. 8A through 8F that are identified by primed reference numerals correspond in objective and function to the similar steps and/or boxes identified by the same unprimed reference number in FIGS. 6A through 6F.

In FIG. 8A the start-up flow chart 300' is essentially the same as the start-up flow chart 300 of FIG. 6A, except for block 400 at the bottom of the drawing. The start-up flow chart includes blocks or steps 301', 302', 303', and 304', which correspond to blocks or steps of the same number from FIG. 6A. The start-up flow chart 300' provides for the obtaining of reference information or a so-called reference database representative of acceptable specifications (or criteria) which are desired to be matched by the sample which is substantially to be examined and compared to the reference.

If the sample intended for examination and comparison is a sample that had been stored, say in a drum, or had been transported from a chemical plant or system to a different place of utilization, such as by tank truck, then the reference data may be the data obtained on that particular sample using the apparatus 1 when the sample originally had been prepared. Accordingly, the start-up flow chart 300' also includes a step 400 at which the residual data file is created for transfer analysis. Such residual data file will contain the information concerning the sample for subsequent comparison with new data obtained on the same sample after storage and/or transport.

Figure 8B:
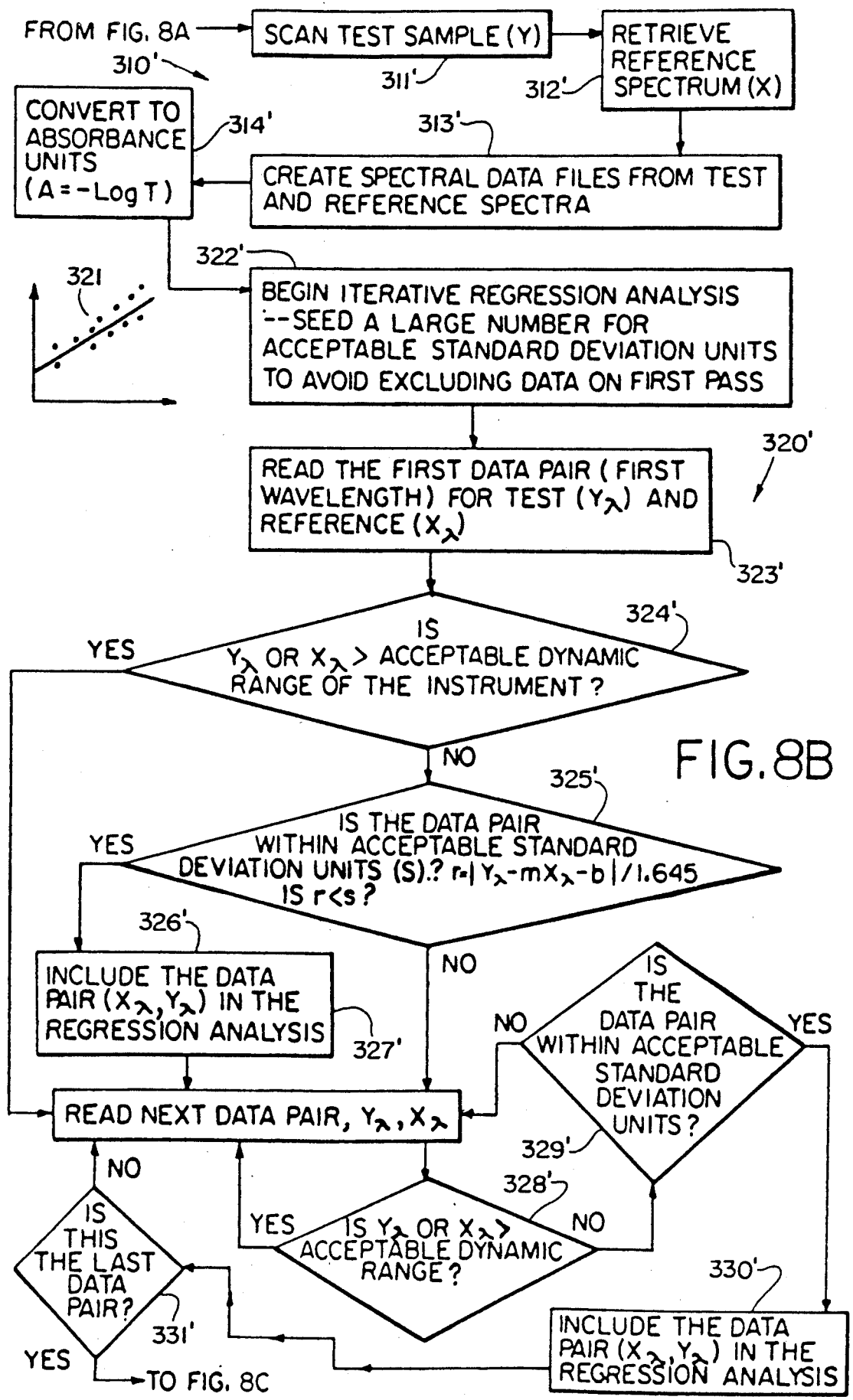

In FIGS. 8B and 8C the sample obtaining flow chart portion 310', which includes blocks 311' through 314', and the iterative regression analysis flow chart portion 320', in which a preferred straight line model 321' is obtained or matched and which includes blocks 322' through 335', are essentially the same in structure and function as the correspondingly numbered flow chart portions illustrated and described above with respect to FIGS. 6B and 6C.

Turning to FIG. 8D1 and 8D2, a flow chart portion 410 and 410' by which a residual spectrum comparing the normalized absorbance data values of the sample at respective wavelengths to the mean value or average normalized data values for of all prior acceptable absorbance values (at such respective wavelengths) previously obtained and stored with respect to other "runs" of the apparatus 1 in order to determine a first set of limits with which to compare the sample absorbance data. Thus, at block 411 an inquiry is made to determine whether the test sample is a transfer sample (e.g., a drum or tank truck sample). If affirmative, then at block 412 the normalized test absorbance values ($Y'_{lambda}$) with which comparisons are to be made subsequently in flow chart 410 are replaced by the residual absorbance values, ($Y'_{lambda} - X_{lambda}$) in which the normalized values $Y'_{lambda}$ are related to the reference absorbance values $X_{lambda}$, wherein the reference absorbance values information are those obtained and saved when the sample was originally made in the chemical system 11, for example. Thus, a replacement of all the normalized absorbance data values for the sample ($Y'_{lambda}$) with the residual value of normalized absorbance data ($Y'_{lambda}$) minus reference absorbance data ($X_{lambda}$).

At block 413 the first data values are read from the database. Those values which are read include the all of the acceptable absorbance values that had been stored in the database for the particular wavelength under consideration during prior acceptable runs of the apparatus 1 for samples that were acceptable and whose data had been stored. This gives an opportunity to compare the current normalized data value with the average of prior data values taken at the same wavelength for samples that are believed to be equivalent or substantially equivalent. If the inquiry at block 411 had been negative, then the block 413 would be reached directly from block 411 without making the replacements called for in block 412.

An average or mean value, $\overline{Y}_{lambda}$, of all the absorbance values at the wavelength under consideration from the database is computed at block 414. Also computed at block 414 is the standard deviation lambda of such absorbance data values at the specified wavelength using well known techniques for computing standard deviation. The functions at blocks 413 and 414 may be combined, for example, if instead of storing all of the absorbance data values one only were to compute the new average or mean value and the standard deviation value (with appropriate information for subsequent calculation thereof) for storage in the database.

At block 415 the difference between the normalized abosrbance data value $Y'_{lambda}$ and the average or means value is calculated, i.e. ($Y'_{lambda} - \overline{Y}_{lambda}$).

Then, at block 416 an inquiry is made to determine whether the difference calculated in block 415 is greater than an acceptance limit. The acceptance limits are those used and described above. For instance, the acceptable limits for this embodiment would be an average value for the difference of $Y'_{lambda}$ and $\overline{Y}_{lambda}$ plus or mninus a standard deviation value. By standard deviation value, it is meant the standard deviation multiplied by a whole nubmer greater than zero. The discussion of acceptance limits for FIG. 6 (i.e. a range of 1 to about 6 times standard deviation) is applicable here, along with the preferred embodiments described above for FIG. 6. In this embodiment an acceptance limit of 3 times standard deviation is most preferred.

If affirmative at block 416, then at block 417 a counter representing the number of high failures is incremented by one, and at block 418 the wave number location at which such high failure occurred is saved into memory, for example, for subsequent consideration to evaluate where there is a problem with the sample. The flow chart flows to block 419 at which an inquiry is made to determine whether the data just under consideration was the last data point. If not, then the flow chart follows to block 420 at which the next data values are read from the database (as in blocks 413 and 414, for example to obtain both the next average or mean value, $Y_{lambda}$, and standard deviation value, lambda, at the next wavelength for consideration), and the flow chart then returns to block 415 for further calculation and analysis.

At block 416 is the answer were negative, then the flow chart would have followed to block 421, where a further inquiry would be made to determine whether the value $Y'_{lambda}$ minus $Y_{lambda}$ is below acceptable limits. If negative, then the flow chart would follow to block 419. If affirmative, then at blocks 422 and 423 a counter indicating the number of low failures is incremented by one and the wave number at which the low failure had occurred is saved for future evaluation as in block 418.

After the foregoing analysis had been made to determine whether there are any high or low failures, then at block 424 (FIG. 8D2) a residual spectrum of the relationship $Y'_{lambda} - \overline{Y}_{lambda}$ is plotted.

Also, at block 425 a limit at each wavelength is plotted.

At block 426 the number of high and low failures saved at blocks 418 and 423 are output, for example, by display on a screen or printing on a paper. This information can be used to indicate whether or not a sample is acceptable and meets the desired quality assurance requirements with respect to a reference with which it had been compared.

Moreover, at block 427, an inquiry is made to determine whether the database information with which the sample had been compared is adequately representative of a reasonable amount of data. In the preferred embodiment, it is desired to provide adequate representation of sample information. If the nubmer of entries is adequate at block 427, then at block 428 the locations of the various high and low failures are output. This information can be used to determine quality or to identify where a problem may exist in a sample, such as if there had been an overheating condition occurring or a contamination of the sample during manufacturing and/or during storage.

The flow chart then follows to block 366' in FIG. 8E. In the flow chart of FIG. 8E the various blocks and functions identified by reference numerals 366' through 369' are the same as those illustrated and designated by the same unprimed reference numeral and described above with reference to FIG. 6E.

Following from the flow chart of FIG. 8E, the flow chart goes to the flow chart portion 480 in FIG. 8F. Specifically, the flow chart portion 480 provides a second comparison of the normalized absorbance values from the sample ($Y_{lambda}$) with respect to the actual data values for the reference ($X_{lambda}$) material the specifications of which are intended to be matched. The primary difference between the flow chart portion 480 of FIG. 8F and the flow chart portion 380 of FIG. 6F is that in the flow chart portion 480 comparison is made with respect to actual reference values, whereas in flow chart portion 380 comparison is made with respect to mean values.

At block 481 in FIG. 8F the first normalized data value, $Y'_{lambda}$, is read. Then at block 482 the difference between the normalized absorbance value for the sample and the actual absorbance value for the reference the specifications of which are intended to be matched is calculated, i.e., $Y'_{lambda} - X_{lambda}$.

At block 483, an inquiry is made to determine if ($Y_{lambda} - X_{lambda}$) is greater than acceptance limits. The acceptance limits are determined as previously described. If affirmative at block 483, then at block 484, then a counter representing the number of high failures is incremented by one and at block 485, the wavenumber location at which such high failure occurred is saved to memory.

The flow chart flows to block 486 where inquiry is made to determine whether the data just under consideration was the last data point. If not, the flow charts follow to block 487 where the next data value for the normalized absorbance value ($Y'_{lambda}$) is read (as in block 481) and the flow chart then returns to block 482 for further calculation and analysis.

At block 483, if the answer were negative, then the flow chart follows to block 488 where an inquiry is made to determine if normalized absorbance value for the sample minus the absorbance value for the reference is less than acceptance limits (the acceptance limits or criteria have been previously discussed). If at block 488, the answer is affirmative, then at block 489 a counter representing the number of low failure is incremented by one, and at block 490, the wavenumber location at which such low failure occurred is saved to memory. The flow chart then follows to block 486 where the inquiry is made to determine if this is the last data pair. If the answer is negative, then the flow chart flows to block 487 and the next data value is read.

If the answer at block 486 is affirmative, then the flow chart follows to block 491 (FIG. 8F2).

At block 491 a residual spectrum of the difference value, ($Y'_{lambda} - X_{lambda}$); is plotted; and at block 492 acceptable limits are plotted.

The number of high and low failures are output at block 493 to be used, for example, to indicate whether the sample is acceptable. If there were too many failures of one type or another or both, then the sample may be rejected, for example. At block 494 an inquiry is made to determine whether adequate spectra are already included in the absorbance database to assure an adequate amount of data for comparison purposes, for example. If affirmative, then at block 495 the location of the high and low failures is output and this information can be used to identify the source of a possible problem with the sample, as was described above with respect to block 428 in FIG. 8D, for example.

From block 495 or from block 494 (if there were not an adequate number of spectra in the absorbance database) the flow chart follows to block 496 where an opportunity is given to select whether the data from the just examined sample should be added to the absorbance values database. The decision may be based on whether the sample is acceptable within the desired specifications, whether it is intended to cause a variation in the database, etc. If affirmative, then at block 497 the absorbance database is updated. At block 498 the flow chart finishes and possible control functions are implemented, for example, to adjust the chemical process occuring in the chemical system 11, to accept or to discard a sample, to deliver the sample for further use, storage, transport, etc., all of which were described above with respect to FIG. 6F.

If at block 496, the answer is negative, then the flow chart follows to block 498 and finishes. Possible control functions as described above maybe implemented. Such finishing may include simply a printing out and/or storing of data obtained in the above-described analysis. Alternatively, and preferably, such finish would include a feedback control of one or more of the flow control valves of FIG. 1 in order to alter the nature of the chemical system 11 and the chemical process/industrial process being carried out therein.

STATEMENT OF INDUSTRIAL APPLICATION

It will be appreciated that the present invention may be used to analYze a chemical sample relative to a similar reference and to control the nature and/or disposition of such chemical sample as a result of such analysis.

We claim:
1. A method of analysis, comprising the steps of:
   (A) examining at least one characteristic of a sample as a function of a variable parameter to obtain data,
   (B) normalizing the sample data with respect to a model by:
      (1) establishing a plurality of data pairs which are characteristic values for the sample and a reference, both established at a single value of the variable parameter;
      (2) performing a regression analysis with the data pairs to obtain normalization parameters by:
         (a) performing a first regression, using all data pairs, to obtain a set of regression parameters;
         (b) determining acceptability of the regression parameters by comparing variability of the data pairs around the model to predetermined variability limits;
         (c) if the regression parameters are not acceptable, excluding data pairs which do not fall within a predetermined statistical limit around the model, and performing a further regression using a diminished set of data pairs to obtain further regression parameters; and
         (d) repeating steps (b) and (c) in an iterative manner until acceptable regression parameters are obtained, or until a predetermined number of iterations are completed, whichever first occurs; and
      (3) using the normalization parameters to normalize characteristic sample values to reference values,
   (C) making a comparison of the normalized sample data with reference data, and
   (D) determining from the comparison quality of the sample.

2. The method as claimed in claim 1, wherein the characteristic in step (A) is radiation transmission, the variable parameter is wavelength and the data are absorbance values.

3. The method of claim 1, where the model in step (B) approximates a straight line.

4. The method of claim 1, where in step (C) the comparison is subtraction.

5. The method of claim 4, where in step (C) the reference data are the average absorbance values in the database.

6. The method of claim 4, where in step (C) the reference data are the absorbance values for a reference sample.

7. The method of claim 1, where in step (C) the comparison is a residual value for the normalized data and the reference data.

8. The method of claim 7, where in step (D) the determining is accomplished by comparison of the residual value with the residual database value.

9. The method of claim 7, where the reference data are absorbance values for a reference sample.

10. The method of claim 1, where in step (C) the comparison is accomplished in regions.

11. The method of claim 10, where, the regions are from about to 1 to about 200 wavenumbers long.

12. The method of claim 11, wherein the regions are from about 5 to about 100 wavenumbers long.

13. The method of claim 2, wherein the wavelength is in a range from about 4000 to about 400 wavenumbers.

14. The method as claimed in claim 13, wherein the range is from about 1900 to about 600 wavenumbers.

15. The method of claim 1, wherein the regression analysis is linear regression analysis.

16. The method of claim 1, where in step (D), the determining is accomplished by comparing the comparison in step (C) with acceptance limits.

17. The method of claim 16, where the acceptance limits are from 1 to about 6 times standard deviation of the reference data.

18. The method of claim 17, wherein the acceptance limits are from about 2 to about 4 standard deviations of the reference data.

19. A method of analysis, comprising the steps of:
   (A) examining the radiation transmission of the sample as a function of wavelength to obtain absorbance data,
   (B) normalizing the sample absorbance data with respect to a model, by:
      (1) establishing a plurality of data pairs which are characteristic absorbance values for the sample and a reference, both established at a single value of wavelength;
      (2) performing a regression analysis with the data pairs to obtain normalization parameters by:
         (a) performing a first regression, using all data pairs, to obtain a set of regression parameters;
         (b) determining acceptability of the regression parameters by comparing variability of the data pairs around the model to predetermined variability limits;
         (c) if the regression parameters are not acceptable, excluding data pairs which do not fall within a predetermined statistical limit around the model, and performing a further regression using a diminished set of data pairs to obtain further regression parameters; and (d) repeating steps (b) and (c) in an iterative manner until acceptable regression parameters are obtained, or until a predetermined number of iterations are completed, whichever first occurs; and (3) using the normalization parameters to normalize characteristic sample values to reference values;

(C) subtracting the noramlized sample data from reference data, and (D) determining quality of the sample.

20. The method, as claimed in claim 19, wherein the wavelength is examined between about 4000 to about 400 wavenumbers.

21. The method as claimed in claim 20, wherein the wavelength is examined between about 1900 to about 600 wavenumbers.

22. The method as claimed in claim 19, wherein the reference data are average absorbance values in the database.

23. The method of claim 19, where in step (C) the reference data are the absorbance values for a reference sample.

24. The method of claim 19, where in step (C) the subtracting is accomplished in regions.

25. The method as claimed in claim 19, wherein the regions are from about 1 to about 200 wavenumbers long.

26. The method of claim 19, wherein the region are from about 5 to about 100 wavenumbers long.

27. The method of claim 19, where in step (D) the determining is accomplished by comparing or subtracting in step (C) where acceptance limits are from 1 to about 6 times standard deviations in the reference data.

28. The method of claim 19, wherein the acceptance limits are from about 2 to about 4 standard deviations of the reference data.

29. A method of analyzing a sample of a chemical mixture, comprising the steps of:

(A) examining infrared light absorption of the sample as a function of wavelength to obtain data, (B) normalizing the sample data with respect to a model by:

(1) establishing a plurality of data pairs which are characteristic values for the sample and a reference, both established at a single value of wavelength;

(2) performing a regression analysis with the data pairs to obtain normalization parameters by:

(a) performing a first linear regression, using all data pairs, to obtain a set of regression parameters;

(b) determining acceptability of the regression parameters by comparing variability of the data pairs around the model to predetermined variability limits;

(c) if the regression parameters are not acceptable, excluding data pairs which do not fall within a predetermined statistical limit around the model, and performing a further linear regression using a diminished set of data pairs to obtain further regression parameters; and (d) repeating steps (b) and (c) in an iterative manner until acceptable regression parameters are obtained, or until a predetermined number of iterations are completed, whichever first occurs; and (3) using the normalization parameters to normalize characteristic sample values to reference values, (C) making a comparison of the normalized sample data with reference data, and (D) determining from the comparison quality of the sample.

* * * * *